(12) United States Patent
Karni et al.

(10) Patent No.: US 8,950,406 B2
(45) Date of Patent: Feb. 10, 2015

(54) METHOD AND APPARATUS FOR LIGHT-BASED HAIR REMOVAL

(75) Inventors: Ziv Karni, Kfar Shmaryahu (IL); Joseph Lepselter, Nordiya (IL)

(73) Assignee: Alma Lasers Ltd., Caesarea (IL)

( * ) Notice: Subject to any disclaimer, the term of this patent is extended or adjusted under 35 U.S.C. 154(b) by 1686 days.

(21) Appl. No.: 12/203,161

(22) Filed: Sep. 3, 2008

(65) Prior Publication Data

US 2009/0254068 A1 Oct. 8, 2009

Related U.S. Application Data

(63) Continuation of application No. PCT/IL2007/000274, filed on Mar. 4, 2007.

(60) Provisional application No. 60/853,428, filed on Oct. 23, 2006, provisional application No. 60/778,403, filed on Mar. 3, 2006.

(51) Int. Cl.
*A61B 19/00* (2006.01)
*A61B 18/20* (2006.01)
(Continued)

(52) U.S. Cl.
CPC ..... *A61B 18/203* (2013.01); *A61B 2017/00154* (2013.01); *A61B 2018/00005* (2013.01); *A61B 2018/00452* (2013.01);
(Continued)

(58) Field of Classification Search
CPC ............... A61B 18/20; A61B 18/203; A61B 2018/00452; A61B 2018/00476; A61B 2018/1807; A61B 2018/00458; A61B 2018/0047; A61B 2018/00636; A61B 2018/00779; A61B 2018/00791; A61N 5/0616; A61N 2005/0643; A61N 2005/0644

USPC .............. 606/3, 8–12, 16–18; 607/88–91, 96, 607/100, 108; 128/898
See application file for complete search history.

(56) References Cited

U.S. PATENT DOCUMENTS

| 5,595,568 A | 1/1997 | Anderson et al. |
| 5,632,741 A | 5/1997 | Zavislan et al. |

(Continued)

FOREIGN PATENT DOCUMENTS

| WO | WO9737602 | 10/1997 |
| WO | WO9927863 | 6/1999 |

(Continued)

OTHER PUBLICATIONS

Non-final rejection for U.S. Appl. No. 12/203,155 (mailed May 7, 2012).

(Continued)

*Primary Examiner* — Ahmed Farah
(74) *Attorney, Agent, or Firm* — Marc Van Dyke; 4th Dimension IP

(57) ABSTRACT

Methods and apparatus for damaging hair follicles using a series of rapidly-delivered low-fluence pulses of coherent or incoherent light are disclosed herein. In some embodiments, the pulses of coherent or incoherent light have a wavelength or wavelengths primarily in the range between 750 nm and 1500 nm. In some embodiments, applied electromagnetic radiation comprising the rapidly-delivered low-fluence pulses is effective for concomitantly heating both the sub-dermal layer (i.e. the dermis) of the tissue and the hair follicles. In some embodiments, the thermal damaging of the hair follicles is useful for facilitating hair-removal.

4 Claims, 9 Drawing Sheets

(51) Int. Cl.
*A61B 17/00* (2006.01)
*A61B 18/00* (2006.01)
*A61B 18/18* (2006.01)

(52) U.S. Cl.
CPC ............. *A61B 2018/00476* (2013.01); *A61B 2018/1807* (2013.01); *A61B 2018/202* (2013.01)
USPC .................................. 128/898; 606/3; 606/9

(56) References Cited

U.S. PATENT DOCUMENTS

| | | | |
|---|---|---|---|
| 5,683,380 A | 11/1997 | Eckhouse et al. | |
| 5,735,844 A | 4/1998 | Anderson | |
| 5,752,948 A | 5/1998 | Tankovich et al. | |
| 6,050,990 A | 4/2000 | Tankovich | |
| 6,080,147 A | 6/2000 | Tobinick | |
| 6,149,645 A | 11/2000 | Tobinick | |
| 6,165,171 A | 12/2000 | Tobinick | |
| 6,168,589 B1 | 1/2001 | Tobinick | |
| 6,168,590 B1 | 1/2001 | Neev | |
| 6,214,034 B1 | 4/2001 | Azar | |
| 6,217,572 B1 | 4/2001 | Tobinick | |
| 6,235,015 B1 | 5/2001 | Mead | |
| 6,273,884 B1 | 8/2001 | Altshuler et al. | |
| 6,383,176 B1 | 5/2002 | Connors | |
| 6,485,484 B1 | 11/2002 | Connors et al. | |
| 6,514,243 B1 | 2/2003 | Eckhouse et al. | |
| 6,544,259 B1 | 4/2003 | Tsaliovich | |
| 6,579,283 B1 | 6/2003 | Tobinick | |
| 6,595,985 B1 | 7/2003 | Tobinick | |
| 6,936,044 B2 | 8/2005 | McDaniel | |
| 7,097,656 B1* | 8/2006 | Akopov et al. | 607/90 |
| 7,250,045 B2 | 7/2007 | Island | |
| 7,291,140 B2 | 11/2007 | MacFarland | |
| 7,494,503 B2 | 2/2009 | McDaniel | |
| 2001/0041886 A1 | 11/2001 | Durkin et al. | |
| 2002/0019624 A1 | 2/2002 | Clement et al. | |
| 2002/0091377 A1 | 7/2002 | Anderson | |
| 2003/0032950 A1* | 2/2003 | Altshuler et al. | 606/9 |
| 2003/0097123 A1 | 5/2003 | Marchitto | |
| 2003/0216795 A1 | 11/2003 | Harth | |
| 2004/0034319 A1 | 2/2004 | Anderson | |
| 2004/0147985 A1 | 7/2004 | MacFarland | |
| 2004/0167501 A1 | 8/2004 | Island et al. | |
| 2004/0230258 A1 | 11/2004 | Altshuler et al. | |
| 2004/0230260 A1 | 11/2004 | MacFarland et al. | |
| 2005/0015077 A1 | 1/2005 | Kuklin | |
| 2005/0107852 A1 | 5/2005 | Levernier | |
| 2005/0143792 A1 | 6/2005 | Jay | |
| 2005/0197681 A1 | 9/2005 | Barolet | |
| 2005/0215987 A1* | 9/2005 | Slatkine | 606/9 |
| 2005/0215988 A1 | 9/2005 | Altshuler | |
| 2006/0200213 A1 | 9/2006 | McDaniel | |
| 2007/0032847 A1 | 2/2007 | Weckwerth | |
| 2007/0049910 A1 | 3/2007 | Altshuler | |
| 2007/0100401 A1 | 5/2007 | Lin | |
| 2007/0191822 A1 | 8/2007 | McDaniel | |
| 2007/0208326 A1 | 9/2007 | Connors | |
| 2007/0270785 A1 | 11/2007 | Jones | |
| 2008/0027518 A1* | 1/2008 | Island et al. | 607/88 |
| 2008/0039826 A1* | 2/2008 | Scheibner | 606/9 |
| 2009/0012585 A1* | 1/2009 | Karni et al. | 607/88 |

FOREIGN PATENT DOCUMENTS

| WO | WO9932193 | 7/1999 |
|---|---|---|
| WO | WO2005079687 | 9/2005 |

OTHER PUBLICATIONS

Applicant response to Non-final rejection for U.S. Appl. No. 12/203,155 (mailed Nov. 6, 2012).
Final rejection for U.S. Appl. No. 12/203,155 (mailed Dec. 20, 2012).
PCT search report for PCT/IL2007/000274 (mailed Jun. 13, 2008).
PCT written opinion for PCT/IL2007/000274 (mailed Jun. 13, 2008).
Office action with response for CN 200780010851.2 (Jan. 12, 2011).
Office action with response for CN 200780010851.2 (Aug. 28, 2012).
Office action with response for CN 200780010851.2 (Dec. 25, 2012).
Office action with response for CN 200780010851.2 (Jun. 18, 2013).
Office action with response for EP 20070713295 (Aug. 4, 2011).
Office action with response for EP 20070713295 (Jun. 25, 2012).
Office action with response for EP 20070713295 (Apr. 16, 2013).
Communication for EP 20070713295 (Jul. 14, 2014).
Office action with response for IL 193734 (Jul. 25, 2013).
Office action with response for CA 2644512 (Jan. 6, 2014).
Selective Photothermolysis: Precise Microsurgery by Selective Absorption of Pulsed Radiation, Author(s): R. Rox Anderson and John A. Parrish, Source: Science, New Series, vol. 220, No. 4596 (Apr. 29, 1983), pp. 524-527, Published by: American Association for the Advancement of Science.

* cited by examiner

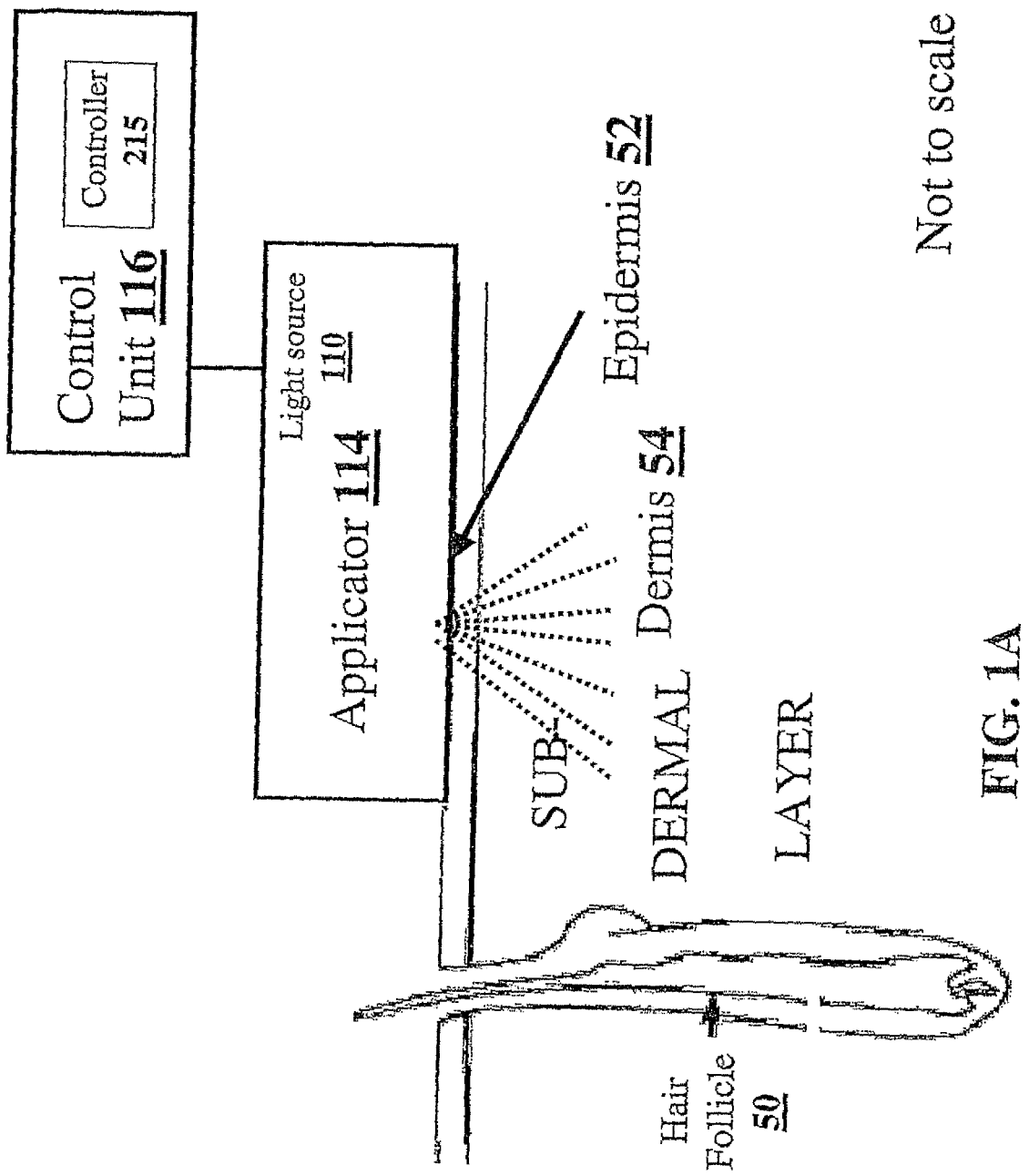

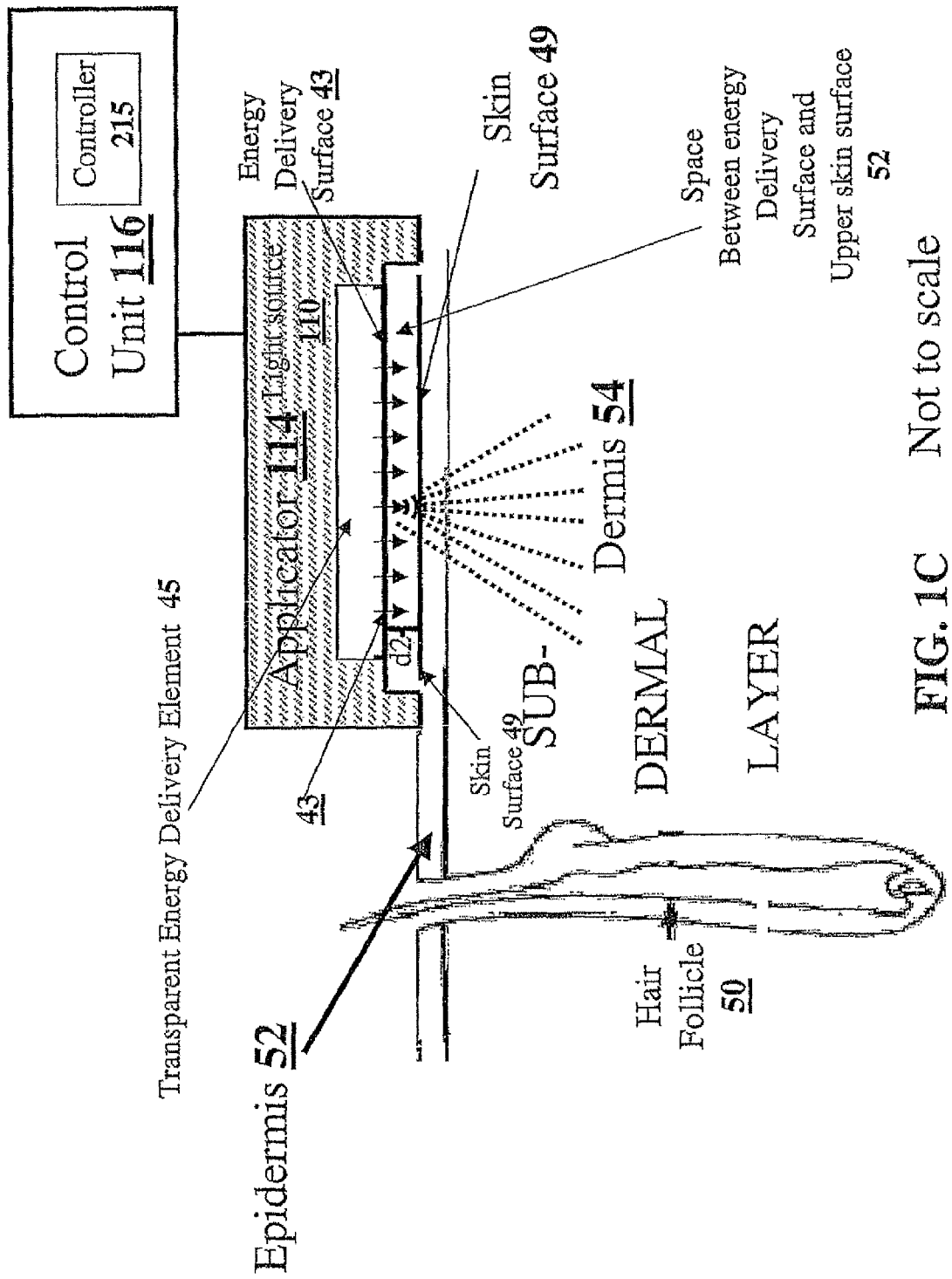
FIG. 1C   Not to scale

| Sub-region 'C' 506 | Sub-region 'D' 508 |
|---|---|
| Sub-region 'B' 504 | Sub-region 'E' 510 |
| Sub-region 'A' 502 | Sub-region 'F' 512 |

Treatment Region 500

FIG. 5A

METHOD AND APPARATUS FOR LIGHT-BASED HAIR REMOVAL

This patent application is a continuation of PCT/IL2007/000274 filed on Mar. 4, 2007, which claims benefit under 119(e) of U.S. Provisional Application No. 60/853,428 filed Oct. 23, 2006, and also claims benefit of U.S. Prov. App. 60/778,403 filed Mar. 3, 2006, all of which are incorporated herein by reference.

FIELD OF THE INVENTION

The present invention relates to methods and apparatus for hair removal using, for example, laser light and/or light from a flash lamp.

BACKGROUND AND RELATED ART

The present disclosure relates to improved methods and apparatus for damaging hair follicles (for example, useful for hair removal) using laser light and/or pulsed incoherent light.

Selective photothermolysis is a surgical method, introduced by Anderson and Parrish in 1983 ("Selective Photothermolysis: Precise Microsurgery by Selective Absorption of Pulsed Radiation", Science, Vol. 220, pp. 524-527), for destroying certain diseased or unsightly tissue, on or near the skin, with minimal damage to the surrounding healthy tissue. The tissue to be destroyed must be characterized by significantly greater optical absorption at some wavelength of electromagnetic radiation than the surrounding tissue. The method consists of irradiating the target and the surrounding tissue with pulsed electromagnetic radiation that is preferentially absorbed by the target. Because the target absorbs the incident radiation much more strongly than the surrounding tissue, the surrounding tissue is usually heated negligibly.

In the past decade, many laser and flash based devices for removing unwanted hair based on the principle of selective photothermolysis have been introduced into the market and to date, this technique is in wide-spread clinical use. During treatment, the skin of the treatment region is irradiated by a beam of light, and the melanin-containing hair follicle absorbs the delivered electromagnetic radiation, resulting in a temperature rise and destruction for the follicle.

Unfortunately, according to this treatment procedure, the light delivered to the treatment region concomitantly heats the nerve-containing melanin-rich epidermis of the patient, and thus, in many clinical situations, light-based hair removal is considered a painful procedure.

There is a widely recognized need for, and it would be highly advantageous to have an improved method and apparatus for hair treatment which heats hair follicles to a sufficient temperature to damage the hair follicles and to facilitate hair removal while delivering a minimal amount of thermal energy to the nerve-containing epidermis. This could be useful for meeting a long felt market need for comfortable hair removal.

The following published patent documents provide potentially relevant background art, and are each incorporated herein by reference in their entirety: US Application 2005/0215988; U.S. Pat. No. 6,485,484; WO 2005/079687; U.S. Pat. No. 6,544,259; U.S. Pat. No. 5,632,741; U.S. Pat. No. 5,752,948; U.S. Pat. No. 6,214,034; U.S. Pat. No. 6,273,884; U.S. Pat. No. 5,683,380; U.S. Pat. No. 6,514,243; US Application 2005/0143792; U.S. Pat. No. 5,735,844; U.S. Pat. No. 5,595,568; US Application 200210019624; US Application 2005/0143792.

SUMMARY

Embodiments of the present invention are based, in part, on the surprising discovery that by rapidly delivering a series of low-fluence light pulses (for example, pulses of coherent light from a laser, or pulses of incoherent light from a flash lamp) to a treatment region of skin, it is possible to remove hair from the treatment region while minimally heating the epidermis.

It is now disclosed for the first time a method of damaging hair follicles in an area of tissue having a plurality of hair follicles, the method comprising: a) applying, to the area of tissue (e.g. to the surface of the tissue), electromagnetic energy comprising a plurality of pulses of coherent light having a wavelength that is at least a minimum wavelength value of at least 750 nm and at most a maximum wavelength value of at most 1500 nm, wherein:
  i) an average pulse fluence of the plurality of pulses is at least a minimum average fluence value that is at least 3 $J/cm^2$ and at most a maximum average fluence value that is at most 20 $J/cm^2$;
  ii) an average repetition rate of the plurality of pulses is at least a minimum repetition value that is at least 5 HZ; and
  iii) an average pulse duration of the light pulses is at least 1 millisecond.

According to some embodiments, the minimum wavelength value is at least 780 nm and the maximum wavelength value is at most 1000 nm.

According to some embodiments, the average pulse duration of the pulses is at least 4 milliseconds.

According to some embodiments, the average pulse duration of the pulses is at least 10 milliseconds.

According to some embodiments, the average pulse duration of the pulses is at most 25 milliseconds.

According to some embodiments, at least 5 pulses are applied at the average repetition rate.

According to some embodiments, at least 15 pulses are applied at the average repetition rate.

According to some embodiments, at least 30 pulses are applied at the average repetition rate.

According to some embodiments, an average power density per square centimeter of the applied electromagnetic energy is at least a minimum average power density value that is at least 50 $Watts/cm^2$.

According to some embodiments, the minimum average power density value is at least 75 $Watts/cm^2$.

According to some embodiments, the minimum average power density value is at least 100 $Watts/cm^2$.

According to some embodiments, the average power density is at least the minimum average power density value during a time period when at least 5 pulses are applied at the average repetition rate.

According to some embodiments, the average power density is at least the minimum power density value during a time period when at least 15 pulses are applied at the average repetition rate.

According to some embodiments, the average power density is at least the minimum power density value during a time period when at least 30 pulses are applied at the average repetition rate.

According to some embodiments, the average power density is at least the minimum power density value during a time period that is at least 1 second.

According to some embodiments, the average power density is at least the minimum power density value during a time period that is at least 2 seconds.

According to some embodiments, the average power density is at least the minimum power density value during a time period that is at least 3 seconds.

According to some embodiments, an average power density of the applied electromagnetic energy is at least at most a maximum power density value that is at most 250 Watts per cm^2.

According to some embodiments, the maximum power density value is at most 150 Watts per cm^2.

According to some embodiments, the average power density is at most the maximum power density value during a time period that is at least 1 second.

According to some embodiments, the average power density is at most the maximum power density value dung a time period that is at least 2 seconds.

According to some embodiments, the average power density is at most the maximum power density value during a time period that is at least 3 seconds.

According to some embodiments, an average power of the applied electromagnetic energy is at least a minimum average power value that is at least 50 Watts.

According to some embodiments, the minimum average power value is at least 75 Watts.

According to some embodiments, the minimum average power value is at least 100 Watts.

According to some embodiments, the average power is at least the minimum average power value during a time period when at least 5 pulses are applied at the average repetition rate.

According to some embodiments, the average power is at least the minimum power value during a time period when at least 15 pulses are applied at the average repetition rate.

According to some embodiments, the average power is at least the minimum power value during a time period when at least 30 pulses are applied at the average repetition rate.

According to some embodiments, the average power is at least the minimum power value during a time period that is at least 1 second.

According to some embodiments, the average power is at least the minimum power value during a time period that is at least 2 seconds.

According to some embodiments, the average power is at least the minimum power value during a time period that is at least 3 seconds.

According to some embodiments, an average power of the applied electromagnetic energy is at least at most a maximum power value that is at most 250 Watts.

According to some embodiments, the maximum power density value is at most 150 Watts.

According to some embodiments, the average power is at most the maximum power value during a time period that is at least 1 second.

According to some embodiments, the average power is at most the maximum power value during a time period that is at least 2 seconds.

According to some embodiments, the average power is at most the maximum power value during a time period that is at least 3 seconds.

According to some embodiments, the minimum repetition value is at least 7.5 HZ.

According to some embodiments, an average repetition rate of the plurality of pulses is at most a maximum repetition value that is at most 20 HZ.

According to some embodiments, the maximum repetition value is at most 15 HZ.

According to some embodiments, the maximum average fluence value is at most 15 J/cm^2.

According to some embodiments, the maximum average fluence value is at most 12.5 J/cm^2.

According to some embodiments, the maximum average fluence value is at most 10 J/cm^2.

According to some embodiments, the minimum average fluence value is at least 5 J/cm^2.

According to some embodiments, the minimum average fluence value is at most 7.5 J/cm^2.

According to some embodiments, a ratio between a pulse fluence standard deviation of the plurality of pulses and the average pulse fluence of the plurality of pulses is at most a standard deviation ratio that is at most 0.5.

According to some embodiments, the standard deviation ratio is at most 0.2.

According to some embodiments, the applied electromagnetic energy is effective to heat the sub-dermal layer of the skin region to a minimum temperature that is least 42 degrees.

According to some embodiments, the minimum temperature is at least 45 degrees.

According to some embodiments, the applied electromagnetic energy is effective to heat the sub-dermal layer of the skin region to a maximum temperature that is most 50 degrees.

According to some embodiments, a ratio between a peak power and an average power of the pulses of coherent light is at least a minimum power ratio that is least 1.5.

According to some embodiments, the minimum power ratio is at least 2.

According to some embodiments, the minimum power ratio is at least 5.

According to some embodiments, a ratio between a peak power and an average power of the pulses of coherent light is at most a maximum power ratio that is most 20.

According to some embodiments, the maximum power ratio is at most 15.

According to some embodiments, the maximum power ratio is at most 10.

According to some embodiments, a peak power of the applied electromagnetic energy is at most a maximum peak power value that is at most 1500 Watts.

According to some embodiments, the maximum peak power value is at most 1000 Watts.

According to some embodiments, a spot area of the coherent light is between 0.5 cm^2 and 2 cm^2.

According to some embodiments, the spot area exceeds 1.2 cm^2.

According to some embodiments, a ratio between the average pulse fluence, and the average repetition rate of the plurality of pulses is at most a maximum ratio value that is at most 3 (J*s)/cm^2;

According to some embodiments, the maximum ratio value is at most 2.5 (J*s)/cm^2.

According to some embodiments, the maximum ratio value is at most 2 (J*s)/cm^2.

According to some embodiments, the maximum ratio value is at most 1.5 (J*s)/cm^2.

According to some embodiments, the maximum ratio value is at most 1 (J*s)/cm^2.

According to some embodiments, a ratio between the average pulse fluence and the average pulse duration is at most a maximum ratio value that is at most 1.5 J/(cm^2*ms).

According to some embodiments, the maximum ratio value is at most 1 J/(cm^2*ms).

According to some embodiments, the maximum ratio value is at most 0.75 J/(cm^2*ms).

According to some embodiments, the area of tissue has a size that is at least 2 cm^2 and at most 1000 cm^2.

According to some embodiments, the step of applying the pulses of coherent light comprises generating the coherent light pulses using a diode laser.

According to some embodiments, the electromagnetic energy is delivered from an applicator located above a surface of the area of tissue such that there is a gap between a lower surface of the applicator and the surface of the area of tissue.

According to some embodiments, the electromagnetic energy is delivered from an applicator comprising: i) a transparent delivery surface; and ii) a spacer housing, the applicator being configured such that upon engagement of applicator to the surface of the area of tissue, the transparent delivery surface is above a surface of the area of tissue.

According to some embodiments, the application of the electromagnetic energy comprising the plurality of pulses is carried out using an applicator moving over the surface of the area of tissue for at least a minimum applicator distance that is at least 2 cm at an applicator velocity that is at least a minimum applicator velocity value that is at least 1 cm/sec and that is at most a maximum applicator velocity value that is at most 20 cm/see.

According to some embodiments, the minimum applicator distance is at least 3 cm.

According to some embodiments, the minimum applicator velocity is at least 3.5 cm/sec.

According to some embodiments, the maximum applicator velocity is at most 10 cm/sec.

According to some embodiments, the maximum applicator velocity is at most 6.5 cm/sec.

According to some embodiments, the method further comprises b) cooling at least a portion of the tissue.

According to some embodiments, the applying of the electromagnetic energy is carried out without cooling the area of tissue.

According to some embodiments, the applying comprises: i) establishing an energy phase wherein a given region having a surface area of 2 cm^2 is subjected the applied electromagnetic energy comprising the plurality pulses applied at the average repetition rate; and ii) immediately after the energy phase, establishing, for the given region, a resting phase having a duration that is at least 2 seconds and at most a maximum resting phase duration that is at most 60 minutes such that during the resting phase, an average power of applied electromagnetic energy having a wavelength of at least 750 nm and at most 1500 nm applied to the area of tissue is at most 30 watts; iii) immediately after the resting phase, repeating steps (a) and (b) to the given region of tissue at least M times, M being an integer whose value is at least one.

According to some embodiments, the resting phase duration is at least 10 seconds.

According to some embodiments, the resting phase duration is at least 30 seconds.

According to some embodiments, the resting phase duration is at least 90 seconds.

According to some embodiments, the resting phase duration is at most 10 minutes.

According to some embodiments, the resting phase duration is at most 5 minutes.

According to some embodiments, M is at least 2.

According to some embodiments, M is at least 3.

According to some embodiments, for each energy phase of a plurality of the resting phase, a cumulative applied energy density of the applied electromagnetic energy for the each energy phase is at least 20 joules/cm^2 and at most 200 joules/cm^2 times within a time period that is at most 20 minutes.

According to some embodiments, the electromagnetic energy comprising the pulses are applied to light colored skin.

According to some embodiments, the electromagnetic energy comprising the pulses is applied to tissue containing low-melanin hair so as to damage the low-melanin hair.

According to some embodiments, the electromagnetic energy comprising the pulses is applied to ski of Fitzpatrick type 1-3 so as to damage hair associated with skin of Fitzpatrick type 1-3.

According to some embodiments, the electromagnetic energy comprising the pulses is applied to skin of Fitzpatrick type 4-6 so as to damage hair associated with skin of Fitzpatrick type 4-6.

According to some embodiments, the electromagnetic energy is applied to the tissue so as to damage low-melanin hair associated with the tissue.

It is now disclosed for the first time a method of damaging hair follicles in an area of tissue having a plurality of hair follicles, the method comprising:
  a) applying, to the area of tissue, electromagnetic energy comprising a plurality of light pulses, each pulse of light comprising primarily one or more wavelength within the range between a minimum wavelength value that is at least 750 nm and a maximum wavelength value that is at most 1500 nm, wherein:
    i) a ratio between an average pulse fluence of the plurality of light pulses and an repetition rate of the plurality of light pulses is at most a maximum ratio value that is at most 3 (J*s)/cm^2; and
    ii) an average pulse duration of the light pulses is at least 1 millisecond.

According to some embodiments, the plurality of light pulses comprises pulses of coherent light having a wavelength within the wavelength range.

According to some embodiments, the plurality of light pulses comprises pulses of incoherent light having wavelengths within the wavelength range.

According to some embodiments, at least 75% of incoherent light of the incoherent light pulses has a wavelength in the range.

According to some embodiments, at least 95% of incoherent light of the incoherent light pulses has a wavelength in the range.

According to some embodiments, the maximum ratio value is at most 2 J/(cm^2*ms).

According to some embodiments, the maximum ratio value is at most 1.5 J/(cm^2*ms).

According to some embodiments, the maximum ratio value is at most 1 J/(cm^2*ms).

According to some embodiments, the maximum ratio value is at most 0.75 J/(cm^2*ms).

It is now disclosed for the first time a method of damaging hair follicles in an area of tissue having a plurality of hair follicles, the method comprising: a) applying, to the area of tissues electromagnetic energy comprising a plurality of light pulses, each pulse of light comprising primarily one or more wavelengths within the range between a minimum wavelength value that is at least 750 nm and a maximum wavelength value that is at most 1500 nm, wherein: i) a ratio between an average pulse fluence of the plurality of pulses and an average pulse duration of the pulses is at most a maximum value that is at most 1.5 J/(cm^2*ms); and ii) an average pulse duration of the light pulses is at least 1 millisecond.

According to some embodiments, the plurality of light pulses comprises pulses of coherent light having a wavelength within the wavelength range.

According to some embodiments, the plurality of light pulses comprises pulses of incoherent light having wavelengths within the wavelength range.

According to some embodiments, at least 75% of incoherent light of the incoherent light pulses has a wavelength in the range.

According to some embodiments, at least 95% of incoherent light of the incoherent light pulses has a wavelength in the range.

According to some embodiments, the maximum ratio value is at most 1 J/(cm^2*ms).

According to some embodiments, the maximum ratio value is at most 0.75 J/(cm^2*ms).

It is now disclosed for the first time a method of damaging hair follicles in an area of tissue having a plurality of hair follicles, the method comprising: a) applying, to the area of tissue, electromagnetic energy comprising a plurality of pulses of coherent light having a wavelength of that is at least a minimum wavelength value of at least 750 nm and at most a maximum wavelength value of at most 1500 nm, wherein: i) an average pulse fluence of the plurality of pulses is at least a minimum average fluence value that is at least 5 J/cm^2 and at most a maximum average fluence value that is at most 20 J/cm^2; ii) an average repetition rate of the plurality of pulses is at least a minimum repetition value that is at least 7.5 HZ; and iii) an average pulse duration of the light pulses is at least 7.5 milliseconds and at most 25 milliseconds; and iv) at least 15 pulses are applied at the average repetition rate.

It is now disclosed for the first time a method of damaging hair follicles in an area of tissue having a plurality of hair follicles, the method comprising: a) applying, to the area of tissue, electromagnetic energy comprising a plurality of pulses of coherent light having a wavelength of that is at least a minimum wavelength value of at least 750 nm and at most a maximum wavelength value of at most 1500 nm, wherein: i) an average pulse fluence of the plurality of pulses is at least a minimum average fluence value that is at least 5 J/cm^2 and at most a maximum average fluence value that is at most 20 J/cm^2; ii) an average repetition rate of the plurality of pulses is at least a minimum repetition value that is at least 7.5 HZ; and iii) an average pulse duration of the light pulses is at least 7.5 milliseconds and at most 25 milliseconds; iv) an average power of the plurality of pulses is at least 60 Watts; and v) at least 15 pulses are applied at the average repetition rate.

It is now disclosed for the first time an apparatus for damaging hair follicles in an area of tissue having a plurality of hair follicles, the apparatus comprising: a) a coherent light source operative to generate coherent light comprising a plurality of coherent light pulses having a wavelength that is at least a minimum wavelength value of at least 750 nm and at most a maximum wavelength value of at most 1500 nm; and b) a controller operative to at least partially control pulse characteristics of the light pulses, the source and the controller being configured such that: i) an average pulse fluence of the plurality of pulses is at least a minimum average fluence value that is at least 3 J/cm^2 and at most a maximum average fluence value that is at most 20 J/cm^2; ii) an average repetition rate of the plurality of pulses is at least a minimum repetition value that is at least 5 HZ; and iii) an average pulse duration of the light pulses is at least 1 millisecond.

According to some embodiments, the minimum wavelength value is at least 780 nm and the maximum wavelength value is at most 1000 nm.

According to some embodiments, the source and the controller are configured such that the average pulse duration of the pulses is at least 4 milliseconds.

According to some embodiments, the source and the controller are configured such that the average pulse duration of the pulses is at least 10 milliseconds.

According to some embodiments, the source and the controller are configured such that the average pulse duration of the pulses is at most 25 milliseconds.

According to some embodiments, the source and the controller are configured to provide at least 5 pulses at the average repetition rate.

According to some embodiments, the source and the controller are configured to provide at least 15 pulses at the average repetition rate.

According to some embodiments, the source and the controller are configured to provide at least 30 pulses at the average repetition rate.

According to some embodiments, the source and the controller are configured to provide the coherent light comprising the plurality of pulses at an average power density per square centimeter that is at least a minimum average power density value that is at least 50 Watts/cm^2.

According to some embodiments, the minimum average power density value is at least 75 Watts/cm^2.

According to some embodiments, the minimum average power density value is at least 100 Watts/cm^2.

According to some embodiments, the source and the controller are configured to provide the average power density per square centimeter that is at least the minimum average power density value when generating at least 5 pulses at the average repetition rate.

According to some embodiments, the source and the controller are configured to provide the average power density per square centimeter that is at least the minimum average power density value when generating at least 15 pulses at the average repetition rate.

According to some embodiments, the source and the controller are configured to provide the average power density per square centimeter that is at least the minimum average power density value when generating at least 30 pulses at the average repetition rate.

According to some embodiments, the source and the controller are configured to sustain the provided average power density per square centimeter that is at least the minimum average power density value for at least 1 second.

According to some embodiments, the source and the controller are configured to sustain the provided average power density per square centimeter that is at least the minimum average power density value for at least 2 seconds.

According to some embodiments, the source and the controller are configured to sustain the provided average power density per square centimeter that is at least the minimum average power density value for at least 3 seconds.

According to some embodiments, the source and the controller are configured to provide the coherent light comprising the plurality of pulses at an average power density per square centimeter that is at most a maximum average power density value that is at most 250 Watts/cm^2.

According to some embodiments, the maximum power density value is at most 150 Watts per cm^2.

According to some embodiments, the source and the controller are configured to sustain the delivery of the average power density per square centimeter that is at least the minimum average power density value for at least 1 second.

According to some embodiments, the source and the controller are configured to sustain the delivery of the average power density per square centimeter that is at least the minimum average power density value for at least 2 seconds.

According to some embodiments, the source and the controller are configured to sustain the delivery of the average power density per square centimeter that is at least the minimum average power density value for at least 3 seconds.

According to some embodiments, the source and the controller are configured to operate at an average power that is at least a minimum average power value that is at least 50 Watts.

According to some embodiments, the minimum average power value is at least 75 Watts.

According to some embodiments, the minimum average power value is at least 100 Watts.

According to some embodiments, the source and the controller are configured to operate at the average power that is at least the minimum average power value during a time period when at least 5 pulses are applied at the average repetition rate.

According to some embodiments, the source and the controller are configured to operate at the average power that is at least the minimum average power value during a time period when at least 15 pulses are applied at the average repetition rate.

According to some embodiments, the source and the controller are configured to operate at the average power that is at least the minimum average power value during a time period when at least 30 pulses are applied at the average repetition rate According to some embodiments, the source and the controller are configured to sustain the average power that is at least the minimum average power value for at least 1 second.

According to some embodiments, the source and the controller are configured to sustain the average power that is at least the minimum average power value for at least 2 seconds.

According to some embodiments, the source and the controller are configured to sustain the average power that is at least the minimum average power value for at least 3 seconds.

According to some embodiments, the source and the controller are configured to operate at an average power that is at most a maximum average power value that is at least 250 Watts.

According to some embodiments, the maximum power density value is at most 150 Watts.

According to some embodiments, the source and the controller are configured to sustain the average power that is at most the maximum average power value for at least 1 second.

According to some embodiments, the source and the controller are configured to sustain the average power that is at most the maximum average power value for at least 2 seconds.

According to some embodiments, the source and the controller are configured to sustain the average power that is at most the maximum average power value for at least 3 seconds.

According to some embodiments, the source and the controller are configured such that the minimum repetition value is at least 7.5 HZ.

According to some embodiments, the source and the controller are configured such that an average repetition rate of the plurality of pulses is at most a maximum repetition value that is at most 20 HZ.

According to some embodiments, the source and the controller are configured such that the maximum repetition value is at most 15 HZ.

According to some embodiments, the source and the controller are configured such that the maximum average fluence value is at most 15 J/cm^2.

According to some embodiments, the source and the controller are configured such that the maximum average fluence value is at most 12.5 J/cm^2.

According to some embodiments, the source and the controller are configured such that the maximum average fluence value is at most 10 J/cm^2.

According to some embodiments, the source and the controller are configured such that the minimum average fluence value is at least 5 J/cm^2.

According to some embodiments, the source and the controller are configured such that the minimum average fluence value is at most 7.5 J/cm^2.

According to some embodiments, the source and the controller are configured such that a ratio between a pulse fluence standard deviation of the plurality of pulses and the average pulse fluence of the plurality of pulses is at most a standard deviation ratio that is at most 0.5.

According to some embodiments, the standard deviation ratio is at most 0.2.

According to some embodiments, the source and the controller are configured to provide the coherent light such that the provided coherent light is effective to heat the sub-dermal layer of the skin region to a temperature that is least minimum temperature of 42 degrees.

According to some embodiments, the minimum temperature is at least 45 degrees.

According to some embodiments, the source and the controller are configured to provide the coherent light such that the provided coherent light is effective to heat the sub-dermal layer of the skin region to a temperature that is most a maximum temperature of 50 degrees.

According to some embodiments, the source and the controller are configured such that a ratio between a peak power and an average power of the coherent light comprising the coherent light pulses is at least a minimum power ratio that is least 1.5.

According to some embodiments, the minimum power ratio is at least 2.

According to some embodiments, the minimum power ratio is at least 5.

According to some embodiments, the source and the controller are configured such that a ratio between a peak power and an average power of the coherent light comprising the coherent light pulses is at most a maximum power ratio that is most 20.

According to some embodiments, the maximum power ratio is at most 15.

According to some embodiments, the maximum power ratio is at most 10.

According to some embodiments, the source and the controller are configured to provide a peak power of the coherent light pulses that is at most a maximum peak power value that is at most 1500 Watts.

According to some embodiments, the maximum peak power value is at most 1000 Watts.

According to some embodiments, the apparatus is operative to provide a spot area of the coherent light is between 0.5 cm^2 and 2 cm^2.

According to some embodiments, the spot area exceeds 1.2 cm^2.

According to some embodiments, the source and the controller are configured such that a ratio between the average pulse fluence and the average repetition rate of the plurality of pulses is at most a maximum ratio value that is at most 3 (J*s)/cm^2.

According to some embodiments, the maximum ratio value is at most 2.5 (J*s)/cm^2.

According to some embodiments, the maximum ratio value is at most 2 (J*s)/cm^2.

According to some embodiments, the maximum ratio value is at most 1.5 (J*s)/cm^2.

According to some embodiments, the maximum ratio value is at most 1 (J*s)/cm^2.

According to some embodiments, the source and the controller are configured such that ratio between the average pulse fluence and the average pulse duration is at most a maximum ratio value that is at most 1.5 J/(cm^2*ms).

According to some embodiments, the maximum ratio value is at most 1 J/(cm^2*ms).

According to some embodiments, the maximum ratio value is at most 0.75 J/(cm^2*ms).

According to some embodiments, the maximum ratio value is at most 0.6 J/(cm^2*ms).

According to some embodiments, the step of applying the pulses of coherent light comprises generating the coherent light pulses using a diode laser.

According to some embodiments, the coherent light source comprises a diode laser.

According to some embodiments, the apparatus filer comprises d) a cooling assembly for cooling at least a portion of the tissue.

According to some embodiments, the cooling assembly is selected from the group consisting of a contact cooling assembly and a spray cooling assembly.

According to some embodiments, the apparatus further comprises: c) an optics assembly for directing the coherent light comprising the coherent light pulses to the area of tissue.

According to some embodiments, the optics assembly comprises a substantially transparent light-delivery element having a substantially-flat light-delivery surface having a surface area of at least 0.8 cm^2.

According to some embodiments, the apparatus further comprises d) an applicator housing for housing the substantially flat light-delivery surface, the applicator configured such that upon engagement of applicator to the surface of the area of tissue, the transparent delivery surface is above a surface of the area of tissue.

It is now disclosed for the first time an apparatus for removing hair from an area of tissue having a plurality of hair follicles, the apparatus comprising:
a) a coherent light source operative to generate coherent light comprising a plurality of coherent light pulses having a wavelength that is at least a minimum wavelength value of at least 750 nm and at most a maximum wavelength value of at most 1500 nm; and
b) a controller operative to at least partially control pulse characteristics of the light pulses, the source and the controller being configured such that:
i) an average pulse fluence of the plurality of pulses is at least a minimum average fluence value that is at least 0.5 J/cm^2 and at most a maximum average fluence value that is at most 20 J/cm^2;
ii) an average repetition rate of the plurality of pulses is at least a minimum repetition value that is at least 5 HZ; and
iii) an average pulse duration of the light pulses is at least 1 millisecond.

It is now disclosed for the first time an apparatus for removing hair from an area of tissue having a plurality of hair follicles, the apparatus comprising:
a) a light source operative to generate light comprising a plurality of light pulses, each pulse of light comprising primarily one or more wavelengths within the range between a minimum wavelength value that is at least 750 nm and a maximum wavelength value that is at most 1500 nm, wherein; and
b) a controller operative to at least partially control pulse characteristics of the light pulses, the source and the controller being configured such that:
i) a ratio between an average pulse fluence of the plurality of light pulses and an repetition rate of the plurality of light pulses is at most a maximum ratio value that is at most 3 (J*s)/cm^2; and
ii) an average pulse duration of the light pulses is at least 1 millisecond.

According to some embodiments, the light source comprises a coherent light source configured such that the plurality of light pulses comprises pulses of coherent light having a wavelength within the wavelength range.

According to some embodiments, the light source comprises an incoherent light source configured such that the plurality of light pulses comprises pulses of incoherent light having wavelengths within the wavelength range.

According to some embodiments, the incoherent light source is configured such that at least 75% of incoherent light of the incoherent light pulses has a wavelength in the range.

According to some embodiments, the incoherent light source is configured such that at least 95% of incoherent light of the incoherent light pulses has a wavelength in the range.

According to some embodiments, the maximum ratio value is at most 2 J/(cm^2*ms).

According to some embodiments, the controller and the light source are configured such that the maximum ratio value is at most 1.5 J/(cm^2*ms).

According to some embodiments, the controller and the light source are configured such that the maximum ratio value is at most 1 J/(cm^2*ms).

According to some embodiments, the controller and the light source are configured such that the maximum ratio value is at most 0.75 J/(cm^2*ms).

It is now disclosed for the first time an apparatus for removing hair from an area of tissue having a plurality of hair follicles, the apparatus comprising: a) a light source operative to generate light comprising a plurality of coherent light pulses having a wavelength that is at least a minimum wavelength value of at least 750 nm and at most a maximum wavelength value of at most 1500 nm; and b) a controller operative to at least partially control pulse characteristics of the light pulses, the source and the controller being configured such that: i) a ratio between an average pulse fluence of the plurality of pulses and an average pulse duration of the pulses is at most a maximum value that is at most 1.5 J/(cm^2*ms); and ii) an average pulse duration of the optical radiation pulses is at least 1 millisecond.

It is now disclosed for the first time a method of damaging hair follicles in an area of tissue having a plurality of hair follicles, the method comprising: a) applying, to the region of skin, electromagnetic energy comprising a plurality of light pulses to heat the sub-dermal layer of the skin region to a first temperature that is least 42 degrees Celsius and less than a thermal destruction temperature of the hair follicles, without heating the epidermis of the skin region to more than a second temperature that is at most 42 degrees Celsius, wherein: i) the applying of the light pulses heats the follicles so that the hairs are removed; ii) an average repetition rate of the pulses is at least 5 pulses/second.

According to some embodiments, the average repetition rate is at least 7.5 pulses/second.

According to some embodiments, the light pulses are coherent light pulses.

According to some embodiments, the first temperature is at least 45 degrees.

It is now disclosed for the first time a method of damaging hair follicles in an area of tissue having a plurality of hair follicles, the method comprising: a) applying, to the region of skin, electromagnetic energy comprising a plurality of light pulses to heat the sub-dermal layer of the skin region to a first temperature that is least 42 degrees Celsius and less than 50 degrees Celsius, without heating the epidermis of the skin region to more than a second temperature that is at most 42 degrees Celsius, wherein: i) the applying of the light pulses heats the follicles so that the hairs are removed; ii) an average repetition rate of the pulses is at least 5 pulses/second.

According to some embodiments, the first temperature is at least 45 degrees.

It is now disclosed for the first time a method of damaging hair follicles in an area of tissue having a plurality of hair follicles, the method comprising: a) applying, to the region of skin, for a time period that is at least 0.5 seconds and at most 20 seconds, electromagnetic radiation comprising a plurality of light pulses to heat the sub-dermal layer of the skin region to a first temperature that is least 42 degrees Celsius and less than 50 degrees Celsius, without heating the epidermis of the skin region to more than a second temperature that is at most 42 degrees Celsius, wherein an average power of the electromagnetic radiation during the time period is at most a maximum average power value that is equal to at most 250 Watts.

According to some embodiments, the first temperature is at least 45 degrees.

According to some embodiments, a duration of the time period is at least 1.5 seconds.

According to some embodiments, a duration of the time period is at least 3 seconds.

According to some embodiments, a duration of the time period is at least 5 seconds.

According to some embodiments, a duration of the time period is at least 10 seconds.

It is now disclosed for the first time a method of damaging hair follicles in an area of tissue having a plurality of hair follicles, the method comprising: a) applying, to the region of skin, for a time period that is at least 0.5 seconds and at most 20 seconds, electromagnetic radiation comprising a plurality of light pulses to heat the sub-dermal layer of the skin region to a first temperature that is least 42 degrees Celsius and less than 50 degrees Celsius, without heating the epidermis of the skin region to more than a second temperature that is at most 42 degrees Celsius, wherein a ratio between a peak power and an average power of the electromagnetic energy during the time period is at least a power ratio that is at least 1.5.

According to some embodiments, the first temperature is at least 45 degrees. According to some embodiments, the power ratio is at least 2.

It is now disclosed for the first time a method of removing low-melanin hair from a region of skin having a plurality of hair follicles, each hair follicle extending into the skin, the method comprising: a) applying, to the region of skin, a plurality of light pulses to heat the sub-dermal layer of the skin region to a first temperature that is least 45 degrees Celsius and less than a thermal destruction temperature of the hair follicles, without heating the epidermis of the skin region to more than a second temperature that is at most 42 degrees Celsius, wherein: i) the applying of the light pulses heats the follicles so that the low-melanin (i.e. blond and/or red and/or grey) hairs are removed; ii) an average fluence of the pulses is at most 20 J/cm^2.

In exemplary embodiments, the pulses are coherent light pulses, and an average fluence of the coherent light pulses is at most 20 J/cm^2.

It is now disclosed for the first time a method of removing hair from a region of skin having a plurality of hair follicles, each hair follicle extending into the skin. The presently-disclosed method comprises a) applying, to the region of skin, a plurality of light pulses to heat the sub-dermal layer of the skin region to a first temperature that is least 45 degrees Celsius and less than a thermal destruction temperature of the hair follicles, without heating the epidermis of the skin region to more than a second temperature that is at most 42 degrees Celsius, wherein: i) the applying of the light pulses heats the follicles so that the hairs are removed; ii) an average repetition rate of the pulses is at least 5 pulses/second.

In exemplary embodiments, an average repetition rate is at least 7.5 pulses/second.

In exemplary embodiments, the light pulses are coherent light pulses.

It is now disclosed for the first time a method of removing hair from a region of skin having a plurality of hair follicles, each hair follicle extending into the skin. The presently-disclosed method comprises a) applying, to the region of skin, a plurality of light pulses to heat the sub-dermal layer of the skin region to a first temperature that is least 45 degrees Celsius and less than a thermal destruction temperature of the hair follicles, without heating the epidermis of the skin region to more than a second temperature that is at most 42 degrees Celsius, wherein: i) the applying of the optical radiation heats the follicles so that the hairs are removed; and ii) a ratio between a peak power and an average power of the light pulses is at least 1.5.

It is now disclosed for the first time apparatus for removing hair from an area of tissue having a plurality of hair follicle. The apparatus comprises a) a source of pulsed radiation for generating a plurality of coherent light pulses; b) an optics assembly (for example, including a wave guide), for example, embedded in an applicator, or a coupler) for directing the generated light pulses to the area of tissue (i.e. via the tissue surface) and c) a controller operative to determine pulse characteristics of the light pulses such that: i) an average pulse fluence of the plurality of pulses is at least a minimum fluence value that is at least 0.5 J/cm^2 and at most a maximum fluence value that is at most 20 J/cm^2; ii) an average repetition rate of the plurality of pulses is at least a repetition value that is 5 HZ; and iii) an average pulse duration of the light pulses is at least 1 millisecond.

According to some embodiments, the apparatus further comprises: d) a cooling assembly for cooling at least a surface of the tissue.

It is noted that some embodiments provide apparatus (for example, including a laser and/or a flash lamp; for example, including a computer controller including electronic circuitry and/or software) for carrying out any presently-disclosed method for hair-removal. In exemplary embodiments, the apparatus is pre-programmed to carry out any treatment protocol (i.e. describing repetition rate and/or fluence of light pulses and/or pulse duration and/or power parameters) described herein.

It is noted that a number of treatment protocols are disclosed herein. It is understood that any device or apparatus that is configured to carry out any of the presently disclosed treatment protocols is within the scope of the present invention.

These and further embodiments will be apparent from the detailed description and examples that follow.

BRIEF DESCRIPTION OF THE DRAWINGS

FIGS. 1A-1C provide block diagrams of exemplary apparatus for damaging hair follicles with electromagnetic radiation in accordance with some embodiments of the present invention.

FIG. 5A provides a block diagram of an exemplary treatment region.

Figure 1B:
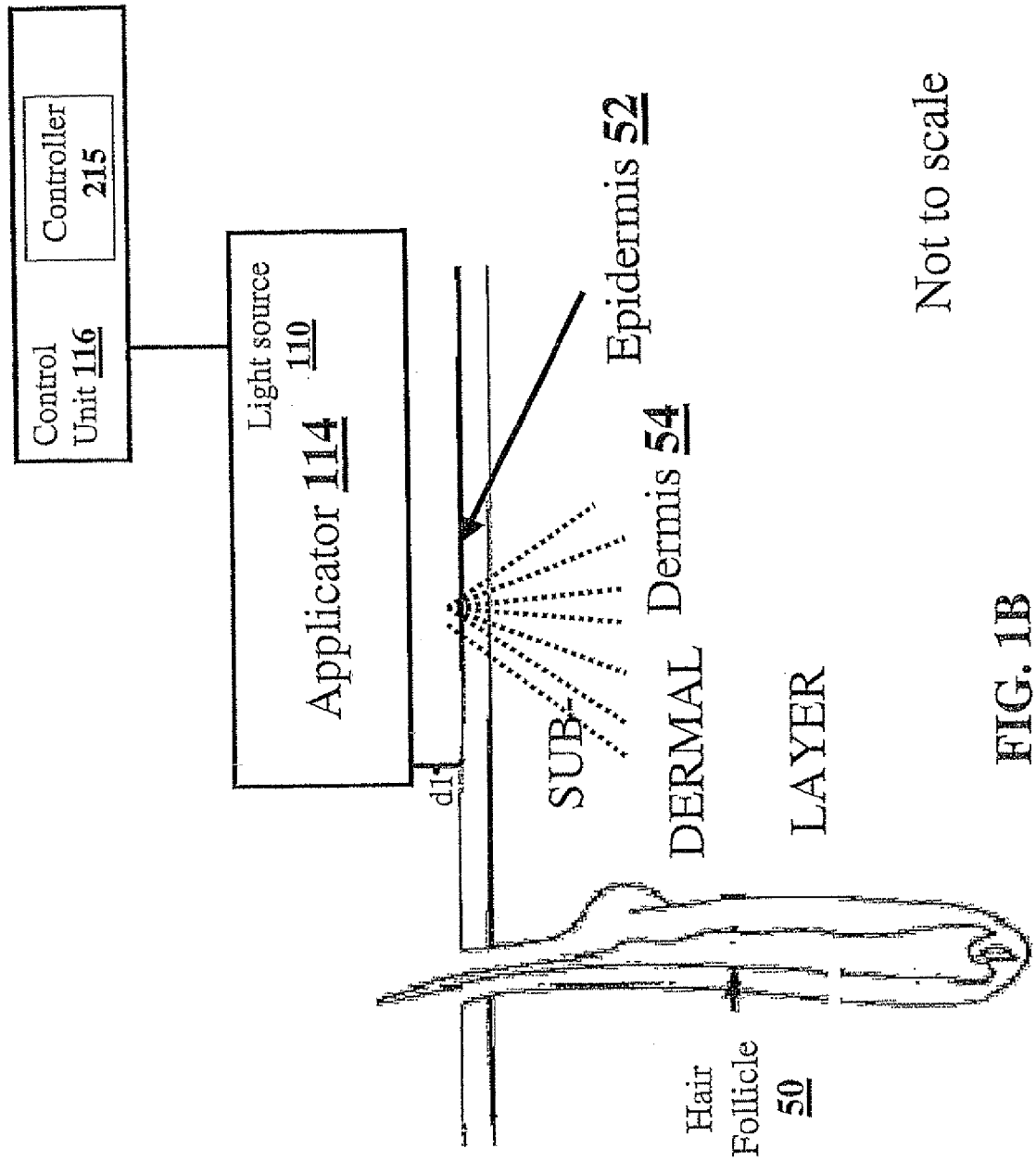

While the invention is described herein by way of example for several embodiments and illustrative drawings, those skilled in the art will recognize that the invention is not limited to the embodiments or drawings described. It should be understood that the drawings and detailed description thereto are not intended to limit the invention to the particular form disclosed, but on the contrary, the invention is to cover all modifications, equivalents and alternatives failing within the spirit and scope of the present invention. As used throughout this application, the word "may" is used in a permissive sense (i.e., meaning "having the potential to"), rather than the mandatory sense (i.e. meaning "must").

DETAILED DESCRIPTION OF EMBODIMENTS

The present invention will now be described in terms of specific, example embodiments. It is to be understood that the invention is not limited to the example embodiments disclosed. It should also be understood that not every feature of the presently disclosed apparatus and method for thermally damaging hair follicles is necessary to implement the invention as claimed in any particular one of the appended claims. Various elements and features of devices are described to fully enable the invention. It should also be understood that throughout this disclosure, where a process or method is shown or described, the steps of the method may be performed in any order or simultaneously, unless it is clear from the context that one step depends on another being performed first.

Introduction and Theoretical Discussion

Embodiments of the present invention are based, in part, on the surprising discovery that by rapidly delivering a series or plurality of low-fluence light pulses (for example, pulses of coherent light from a laser, or pulses of incoherent light from a flash lamp) to a treatment region of skin, it is possible to effectively damage hair follicles in the treatment region while minimally heating the epidermis. It is noted that the aforementioned hair follicle-damaging technique may be useful for safely facilitating the removal of hair from the treatment region of skin.

In particular, and not wishing to be bound by theory, it is noted that even though each individual low-fluence pulse provides only a relatively 'low' peak power, the rapidly-delivered plurality of low-fluence pulses, collectively, may deliver a relatively 'high' average power over enough time to heat the thermally-conductive sub-dermal layer or dermis to a sufficient temperature (for example, at least 42 degrees or at least 45 degrees) to damage hair follicles to an extent necessary to facilitate hair removal.

Once again not wishing to be bound by theory, it is postulated that because the dermis is a good heat conductor, when the pulses are rapidly delivered at the 'high repetition rate,' (i) the temperature of the hair follicle does not drop below the temperature of the heated dermis (i.e. the heated-dermis temperature) for a period of time long enough to damage the hair follicle (ii) this heat damaging of the hair follicle is useful for facilitating hair removal.

It is noted that it may be useful to use light in a certain range of wavelengths in order to heat and damage hair follicles (i.e. in a manner useful for hair). Thus, in some embodiments, the optical radiation of the rapidly-delivered low-fluence pulses includes light in the "optical window" having a wavelength of between 750 nm and 1500 nm (or between 780 nm and 1000 nm), which penetrates below the epidermis and to deliver energy to the sub-dermal tissue layer (i.e. the dermis) below the epidermis.

Not wishing to be bound by theory, it is noted that light in this 'optical window' may heat the epidermis less than light, for example, in the range between 650 nm and 700 nm or other ranges. Thus, rather than by relying exclusively on selective photothermolysis to heat the melanin rich hair follicle, it is possible to use the chromophores in the surrounding tissue as 'reservoirs' to effectively heat up and damage the hair follicle.

In some embodiments, one or more of the following features may be provided for the specific case of coherent light:
  i) a total average power density of the delivered optical radiation (for example, coherent light) that is at least 35 Watts/cm$^2$, or at least 50 Watt/cm$^2$, or at least 75 Watts/cm$^2$ This 'high average power' may be sustained for a sufficient 'exposure' time (for example, at least 0.5 seconds, or longer, such as at least 1 second or at least 2 seconds or longer) to heat the sub-dermal tissue (or dermis) in the region of a given hair follicle to at least 42 or at least 45 degrees;
  ii) a ratio between a peak power and the aforementioned average power of the coherent light that is at most 20 or at most 10 (for the case of treatment of with coherent light such as laser light). This may be useful for avoiding a situation where hair is carbonized and/or where the epidermis is heated more than necessary.
  iii) 'rapid pulsing' where the repetition rate of the light pulses (for example, coherent light pulses) that is at least 3.5 pulses/second, or at least 5 pulses/second, or at least and at most 7.5 pulses/second;
  iv) an average fluence (i.e. averaged over individual pulses) of the rapidly-delivered plurality of light pulses (for example, coherent or incoherent light pulses) that is at least 3 J/cm$^2$ (or at least 5 J/cm$^2$) and at most 20 J/cm$^2$ (or at most 15 J/cm$^2$); and
  v) an average pulse duration or 'pulses width' of individual pulses of plurality of light pulses (i.e. the 'short pulses') (for example, coherent or incoherent) is at least 3 milliseconds and at most 25 milliseconds, for example, between, 10 milliseconds and 20 milliseconds or the case of coherent light. For the case of incoherent light, different pulse width (for example, shorter pulse widths) may be provided.

For the case of incoherent light, different features and values may be provided, though, in exemplary embodiments, a series of relatively 'low fluence' pulses of incoherent light may be delivered at a relatively 'rapid' repetition rate.

The teachings provided by embodiments of the present invention are applicable both for coherent-light devices and protocols (for example, using a laser including but not limited to a diode laser) and incoherent-light devices and protocols (for example, using filtered broadband light).

It is noted that the teachings of the present invention may be used to remove hair from any area of the body, including but not limited to the back, face, head, eyebrows, eyelashes, chest, abdomen, pubic area, legs, and armpits.

Furthermore, it is noted that application or delivery of light, for example one or more pulses of light, to a given region or sub-region or area of tissue (for example skin) refers to application or delivery of the light (for example, one or more pulses of light) to any location or locations with the region or sub-region of tissue.

Optical Radiation and Pulse Properties

Various embodiments of the present invention provide any combination of the following salient features. It is appreciated that not every one of these following features must be included in every embodiment.

a) Wavelength Features.

The present inventor is disclosing a treatment and device that delivers, to the skin of the patient, optical radiation including "deeper-penetrating" optical radiation which traverses the melanin-rich epidermis and is absorbed by the sub-dermal tissue (i.e. the dermis). In some embodiments, this deeper-penetrating optical radiation comprises light having a wavelength between a minimum wavelength value (for example, 750 nm for example 780 nm or 800 nm) and an maximum wavelength value (for example 950 nm, or 980 nm, or 1000 nm, or 1200 nm 1500 nm). Not wishing to be bound by theory, it is disclosed that choosing wavelengths in the "optical window" may be useful for providing a treatment protocol (or treatment device) that is less likely to heat the nerve-containing epidermis, thereby obviating (but not necessarily eliminating) the need for tedious cooling (applied concomitantly, or applied using a "pre-cooling protocol") and/or thereby providing a safer treatment protocol.

In exemplary embodiments related to treatment of tissue with a laser, this is provided, for example, by using a semiconductor diode laser having a wavelength of about 810 nm, though other laser devices are within the scope of the present invention.

In exemplary embodiments related to incoherent light, this is provided by providing light at a plurality of frequencies (for example, light from an IPL device that is filtered with a band-pass filter), such that a majority (or greater) of the of the applied optical radiation has a wavelength in a given wavelength range defined by a minimum wavelength value (for example, 750 nm, for example 780 nm or 800 nm) and an maximum wavelength value (for example 950 nm, or 980 nm, or 1000 nm, or 1200 nm 1500 nm).

In some embodiments, the applied incoherent light and/or each pulse thereof comprises 'primarily' wavelengths win the range defined by the minimum wavelength value and the maximum wavelength value—i.e. at least 70% of the incoherent light or each pulses thereof has a wavelength in this range.

In some embodiments, at least 75% of the incoherent light or each pulses thereof has a wavelength in this range.

In some embodiments, at least 90% of the incoherent light or each pulses thereof has a wavelength in this range.

In some embodiments, at least 95% of the incoherent light or each pulses thereof has a wavelength in this range.

b) Fluence Features.

The present inventor is disclosing for the first time, that it is possible to remove hair by applying low-fluence pulses to the skin of a patient. The particular fluence values may differ in accordance with whether laser light or incoherent light is applied to the tissue to damage the hair follicles.

In exemplary embodiments where the applied optical radiation is from a laser, the "low-fluence" pulses are, on average, at most 20 J/cm^2 per pulse, or at most 15 J/cm^2 per pulse or at most 12.5 J/cm^2 per pulse or at most 10 J/cm^2 per pulse. In exemplary embodiments where the applied optical radiation is from a laser, the "low-fluence" pulses are at least 0.5 J/cm^2 or at least 3 J/cm^2, or at least 5 J/cm^2.

It is appreciated that when a plurality of series of pulses are applied, not every individual pulse necessarily has the same exact fluence, and that there may be some variation in the fluence between pulses.

In some embodiments, however, every pulse of a given plurality (for example, at least 3 or at least 5 or at least 15 or at least 30) of pulses has a fluence in a range disclosed for 'average pulse fluence'—e.g. for the case of coherent or laser light every pulse of a given plurality has a fluence less than 20 J/cm^2 or less than 15 J/cm^2 or less than 12.5 J/cm^2. In an example related to incoherent light (for example from a flash lamp), every pulse of the series or plurality of pulses has a fluence less than 10 J/cm^2, or 8 J cm^2, etc.

It is noted that the specific fluence (as well as other features such as pulse width, repetition rate, power, etc) provided may depend on a number of physiological factors, including but not limited to the skin color and hair color. For example, for lighter hair (less "melanized" hair), it may be desirable to choose a larger fluence. Similarly, for darker skin, it may be desirable to choose a smaller fluence.

It is noted that these low-fluence pulses are surprisingly effective for hair removal.

c) Repetition Rate Features

The present inventor is disclosing for the first time, a hair-removal protocol and device where light is applied to the skin with a certain "high" repetition rate.

As used herein, a 'repetition rate' refers to rate of individual pulses (i.e. in pulses per second, or HZ) delivered over a given time period—the number of pulses delivered or delivered or provided divided by the length of 'given' time period. In different embodiments, the given time period may be, for example, at least 0.5 seconds, at least 1 second, at least 1.5 seconds, at least 2 seconds, at least 3 seconds, at least 5 seconds or at least 10 seconds.

In exemplary embodiments where the applied optical radiation is from a laser, the repetition rate is at least 5 pulses/see, and/or at least 7.5 pulses/sec, and/or at least 10 pulses/sec. In exemplary embodiments where the applied optical radiation is from a laser, the repetition rate is at most 25 pulses/sec, and/or at most 20 pulses/sec, and/or at 15 pulses/sec.

d) Pulse Duration/Pulse Width Features.

In exemplary embodiments where the applied optical radiation is coherent light (for example, from a laser such as a diode laser), the pulse duration (i.e. duration of individual pulses) is at least 3 milliseconds and/or at least 5 milliseconds and/or at least 10 milliseconds and/or at least 15 milliseconds. In exemplary embodiments where the applied optical radiation is from a laser, the pulse duration is at most 30 milliseconds and/or at most 25 milliseconds and/or at most 20 milliseconds.

It is noted that the specific fluence, and also the specific pulse-duration or pulse-width provided may depend on a number of physiological factors, including but not limited to the skin color and hair color. For example, for lighter hair (less "melanized" hair), it may be desirable to choose a longer pulses with a larger fluence. Similarly, for darker skin, it may be desirable to choose shorter pulses with a smaller fluence.

e) Relation Between Fluence and Pulse Duration and/or Peak Power—

In exemplary embodiments, the low fluence pulses may be relatively "broad, flat" pulses that are applied over a minimum period of time with a maximum peak power. In one example related to laser pulses, a pulse having a fluence of at least 10 J/cm^2, is delivered over period of at least 22 milliseconds Thus, in exemplary embodiments related to laser pulses, the ratio between the fluence and the pulse duration is at most 1.5 J/(cm^2*ms), and/or at most 1 J/(cm^2*ms), and/or at most 0.7 J/(cm^2*ms)M, and/or at most 0.5 J/(cm^2*ms)

f) Relation Between Fluence and Repetition—

In exemplary embodiments, a "rapidly applied series of low-fluence pulses" of light are applied. Thus, in exemplary embodiments, a ratio between an average pulse fluence of the plurality of light pulses and an repetition rate of the plurality of light pulses is at most a maximum ratio value that is at most 3 (J*s)/^2, or at most 2 (J*s)/cm^2, or at most 1.5 (J*s)/cm^2.

g) Average Power Features.

In some embodiments, a minimum average power is provided (i.e. incoherent and/or coherent light is delivered at a minimum average power), in order to ensure that the subdermal layer (i.e. the dermis) (or portion thereof) is heated above the minimum dermis heated temperature. For example, a minimum average power density of 35 Watts/cm^2, or 50 Watts/cm^2 is provided for a given period of time (i.e. enough time to heat the dermis to at least 42 or 45 degrees Celsius).

Not wishing to be bound by theory, it is noted that by operating at a relatively 'high' average power for a certain given period of time (for example, at least 0.5 seconds, or at least 1 second, or at least 2 seconds, etc—or a period of time during which a certain minimum number of pulses are delivered—for example at least 3, 5, 10, 15 or 30 pulses), it is possible to provide enough power to heat the sub-dermal layer or dermis.

In some embodiments, a maximum average power is provided (and/or a maximum average power of light in certain wavelengths, for example, in order to a provide a safer treatment and/or a treatment where there is less of a need to cool the dermis. Thus, in exemplary embodiments, the average power is less than 400 Watts, or less than 300 Watts or less than 200 Watts or less than 150 Watts.

h) Ratio of Peak Power to Average Power Features.

The present inventor is disclosing a treatment and device that delivers optical radiation whose intensity varies in time so as to heat the sub-dermal tissue (i.e. the dermis) of the patient. In some embodiments, this is provided by applying optical radiation of an appropriate wavelength with a time-varying profile intensity where the ratio between the peak power of the applied radiation and the average power of the applied radiation is at most a first ratio value and, optionally, at least a second ratio value. Examples of first ratio values and second ratio values provided by different embodiments are listed below.

Not wishing to be bound by theory, it is noted that for many situations where the ratio is greater the second ratio, the applied optical radiation may by characterized by short intense pulses delivered at low frequencies, which, even for wavelengths in the "optical window," may, nevertheless (due to the intense bursts of energy to which the skin is subjected) heat the epidermis (especially, but not exclusively in darker-skinned patients) more than it desired, requiring a greater cooling to provide a safe hair-removal procedure. Thus, by avoiding these intense pulses (i.e. by avoiding intense pulses that cause the ratio between the peak power and the average power to exceed the specified ratio value), it is possible, in exemplary embodiments, to provide a treatment which is less likely to ablate or singe the epidermis and/or the hair shaft.

Thus, in some embodiments (for example, where the applied optical radiation is from a coherent light source including but not limited to a diode laser having a wavelength of 810 nm), this second ratio value is, for example, at most 20, or at most 15, or at most 12, or at most 10.

Furthermore, it is noted that when the ratio between the peak power and the average power approaches unity, the device becomes a CW device rather than a device which delivers pulsed radiation. In exemplary embodiments, the presently disclosed device provide does indeed provide radiation whose intensity varies in time—this may be useful, for example, for localizing at least some of the delivered energy to the hair follicle.

Thus, in some embodiments (for example, where the applied optical radiation is from a coherent light source including but not limited to a diode laser having a wavelength of 810 nm), this first ratio value is, for example, at least 1.2, at least 1.5, at least 2, and/or at least 3. It is noted that having the first ratio value exceed 1 is a salient feature of pulsed energy devices, in contrast to exclusively CW devices, where the ratio is unity.

In different embodiments, at least 30% or at least 50% or at least 70% or at least 90% of delivered electromagnetic energy (or the delivered electromagnetic energy in one or more specified wavelength ranges described herein) is provided as pulses of coherent and/or incoherent light.

According to some embodiments, a ratio between a peak power and au average power of the applied pulses of coherent light is at least a power ratio that is least 1.5 (for example, at least 1.5, at least 2.5, at least 5).

According to some embodiments, a ratio between a peak power and an average power of the applied pulses of coherent light is at most a power ratio that is most 20 (for example, at most 15, or at most 12).

Exemplary Treatment Device

FIGS. 1A-1C provides block diagrams of exemplary devices in accordance with exemplary embodiments of the present invention. These figures (and all figures) are intended as illustrative and not as limiting.

The device includes a source of pulsed light 110 (a source of incoherent light such as a flashlamp and/or a source of coherent light such as a laser), a controller 215 (in the specific example of the figures, provided as part of control unit 116) and an applicator 114.

Applicator 114 is adapted to deliver light to the treatment area of the patient. In some embodiments, applicator 114 includes a housing with an aperture for delivering the pulses of light. In some embodiments, a control may be provide for determining or controlling the applicator size.

It is noted that applicators 114 for delivering optical radiation to skin to remove hair are well-known in the art, and that any known applicator 114 and any known applicator feature may be used in the presently-described apparatus for hair removal.

In some embodiments, the applicator may include and/or be associated some sort of embedded control for example, a button, for controlling the delivered radiation—for example, an 'on/off' control.

Although the applicator 114 is shown in contact with the skin (i.e. in contact with the epidermis 52) in FIG. 1A, this is not to be construed as a limitation, and embodiments where light is applied to the skin without touching the skin are also within the scope of the present invention.

In FIG. 1B, the applicator 114 is 'above' the surface of the skin (i.e. not touching the skin) such that there is a gap of length d1 between the bottom of the applicator 114 and the surface of the skin.

In FIG. 1C, the applicator 114 includes a transparent energy delivery element 45 through which coherent and/or incoherent light (and optionally other electromagnetic energy) is applied to the skin surface 49. The energy delivery element 45 is configured in the applicator 114 such that is a 'spacer' or 'gap of length d2 between the lower surface (or energy delivery surface 43) of transparent energy delivery element 45 and the skin surface.

As shown in FIGS. 1A-1C the control unit 116 includes controller 215 (for example, either (i) automatic electronic controls for example including a microprocessor and/or code provided using any combination of software and hardware and/or (ii) manual controls) controls various parameters of the electromagnetic radiation emitted by the pulsed light source 110.

Thus, it is noted that in the specific example of FIGS. 1A-1C and FIG. 2, controller 215 is provided separately (and in a separate unit) from light source 110 and applicator 114. This is not to be construed as a limitation. In some embodiments, the 'controller' 215 may be configured as an integral part of the light source 110 or as an integral part of a laser or flash device (i.e. including light source 110)—i.e. a light source configured inherently to generate the desired pulse sequence. Furthermore, there is no requirement of a separate 'control unit 116.'

In the example of FIGS. 1A-1C the pulse light source 110 is embedded with applicator 114. Alternatively or additionally, in some examples, the pulse light source 110 is located outside of applicator 114 and the light is delivered, for example via some sort of waveguide or conduit, from an 'external' light source into the applicator 114.

In exemplary embodiments, the 114 applicator is cooled to provide cooling such as contact cooling (for example, contact cooling such as sapphire contact cooling) provided using the applicator. In embodiments related to contact cooling, it may be preferred to provide good thermal contact.

It is appreciated that although there is no cooling requirement, that any combination of cooling techniques may be used, including pre-cooling, concurrent cooling, spray cooling, gel cooling, air cooling, etc.

It exemplary embodiments, the cooling is applied before and/or during and/or after treatment with light pulses. In exemplary embodiments, the amount of cooling (for example, contract cooling and/or spray cooling or any other cooling) is determined by the control unit 116 (for example, controller 215), for example, in accordance with one or more parameters of the pulsed light.

In exemplary embodiments, the light penetrates to the dermis 54 to heat the dermis, for example, to at least 42 degrees or at least 45 degrees Celsius. In exemplary embodiments, the hair follicle 50 is heated to a greater temperature than the temperature of the dermis, for example, to a thermal denaturation temperature, though this is not a requirement and it may be possible to damage hair follicles without necessarily heating the follicles to a denaturation temperature.

Not wishing to be bound by theory, it is noted that in exemplary embodiments, because of the warm temperature of the dermis, the hair follicle does not cool below the temperature of the dermis for a certain period of time. When this happens, the hair can be removed, for example, by waiting for the hair to shed and/or with a tweezer, etc.

In some embodiments, the heated region of dermis (or sub-dermal layer) as an area that is at least 20% or at least 50% or at least 80% any spot area disclosed herein and is heated for a minimum period of time—for example, at least 0.5 second, at least 1 second, at least 2 seconds, or any other period of time useful for achieving the desired heating of the hair follicles (and thermal damage of the hair follicles).

Figure 2:
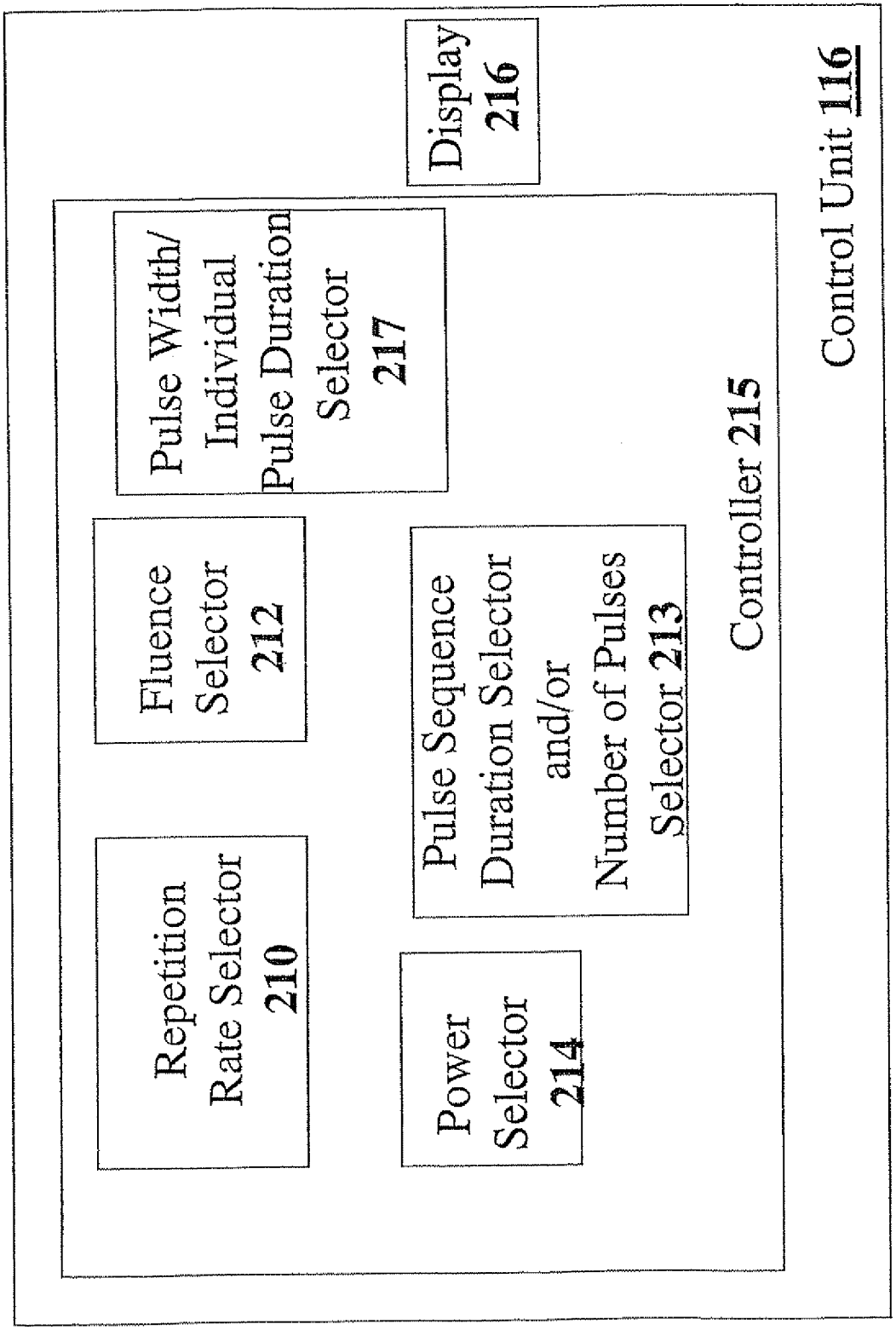
FIG. 2 provides a block diagram of an exemplary control unit.

FIG. 2 provides a block diagram of an exemplary control unit 116. As noted earlier, various parameters may be determined either manually by the operator and/or may be computed using electronic circuitry. It may, nevertheless, be convenient to provide certain 'pre-programmed options.'

Control unit 116 of the example of FIG. 2 includes controller 215. Controller 215 is operative to at least partially control one or more pulse characteristics including but not pulse fluence, duration of individual pulses (i.e. pulse width), power parameters (for example, average and/or peak power), duration of a pulse sequence, number of pulses in a pulse sequence, and pulse rate.

Thus, in the example of FIG. 2, controller 215 includes one or more of: a repetition rate selector 210, fluence selector 212, individual pulse duration (or pulse width) selector 217, power selector 214 (for determining, for example, peak power and/or average power and/or a derived parameter of the two), and a pulse sequence duration selector and/or number of pulses in a pulse sequence selector 213.

Thus, in different embodiments, controller 215 may be operative or programmed to provide a certain pulse sequence comprising at least a minimum number of pulses (for example, at least 3 pulses, at least 5 pulses, at least 10 pulses, at least 15 pulses or at least 30 pulses) at a given repetition rate.

In some embodiments, the control unit 116 is 'pre-configured' to provide a selected treatment protocol for hair removal (for example, any treatment protocol described describing repetition rate and/or fluence of light pulses and/or pulse width of pulse duration and/or power parameters) described herein. In one example, the user may select a given treatment protocol (for example, a presently disclosed protocol) from a plurality of protocols using some sort of used interface (not shown) that utilizes display 216.

In some embodiments, more than one 'program' associated with a given pulse sequence is provided, and a mechanism for selecting a specific program is provided. In one particular example, a user interface for selecting a specific program in accordance with skin and/or hair color is provided.

For example, a 'light skin' program may provide higher fluence pulses, while a 'lower skin' program may provide lower fluence pulses, but, for example, a higher repetition rate.

In exemplary embodiments, the control unit includes a user display for example, useful for selecting a program.

It is noted that in some embodiments, a user may specify a first parameter or set of parameters (for example, a fluence) and controller 215 may determine or calculate another parameter (for example, repetition rate) from the specified parameter or parameters.

It is noted that as depicted in the figures, the light source 110 is 'embedded' in the applicator (for example, handpiece). This salient feature is provided by certain embodiments, though this is not to be construed as a limitation.

In exemplary embodiments, one or more user input controls (for example, keyboard, foot pedal, etc) (not shown) may be provided.

Figure 3:
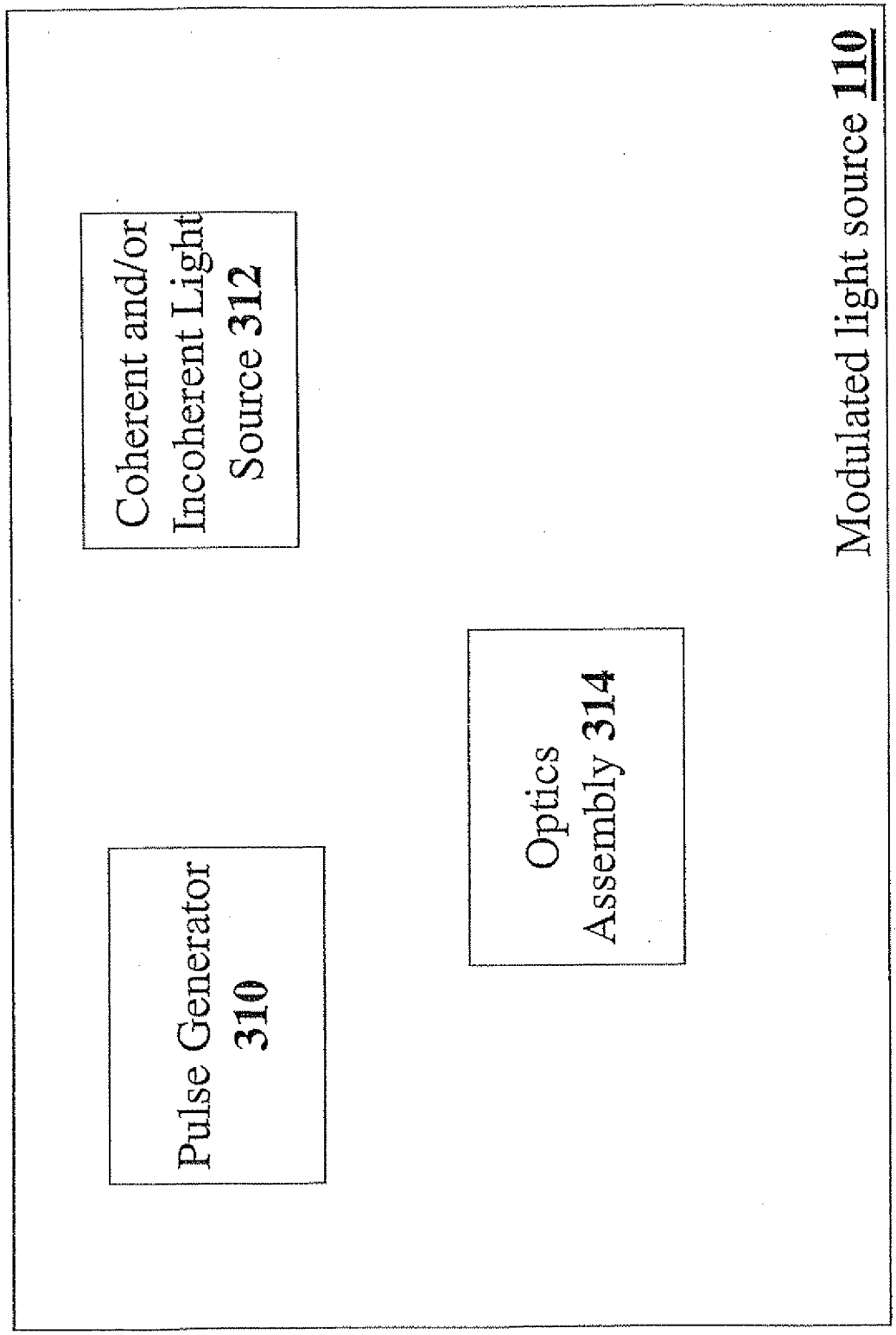
FIG. 3 provides a block diagram of an exemplary pulsed-light source.

FIG. 3 provides a diagram of an exemplary light source 110 (i.e. source of pulsed and/or CW light). In the example of FIG. 3, this includes a pulse generator 310 (for example, controlled by the device control unit), a light source 312 (for example, a laser and/or a source of incoherent light such flash lamp), and an optics assembly 314.

Optics assembly 314 is configured to modify propagation of the electromagnetic radiation of the coherent and/or incoherent light—for example, to direct light in a pre-determined direction and/or to a predetermined location. Optics assembly may include any appropriate optical components known to one skilled in the art for performing this function, including but not limited to wave guides, lenses (i.e. including but not limited to refractive and diffractive lenses), and mirrors. Optionally, in some embodiments related to incoherent light-based hair removal, optics assembly 314 may include a band pass filter, for example, a low-pass filter for filtering incoherent light from the flashlamp.

The flash lamp or other incoherent light source may be programmed to provide light of different ranges of wavelengths.

It is noted that there is no limitation on the shape of the light pulse. In exemplary embodiments, the shape of the pulse is square, though this is certainly not a limitation, and pulses of any shape (for example, sinusoidal, sawtooth, etc) are within the scope of the present invention.

It is noted that both coherent light (i.e. from a laser) and incoherent light (i.e. from a flash-lamp) are within the scope of the present invention. Typically, the spot area will be greater for the incoherent light. Thus, in exemplary embodiments relating to lasers, the spot area is between, for example, 0.5 cm^2 and 2 cm^2. In exemplary embodiments relating to incoherent light, the spot area is between, for example, 3 cm^2 and 10 cm^2—for example, between 3 cm^2 and 7 cm^2.

In some embodiments, the inter-pulse time is maintained constant. Alternatively, this parameter may be varied, providing varying repetition rates.

One salient feature provided in some embodiments by the control unit, is that the pulses of light may be of different predetermined optical radiation and/or pulse parameters, for example, predetermined wavelengths, fluence, repetition-rate, pulse shape, etc.

It is noted that in some embodiments, electromagnetic radiation other than optical radiation (for example, RE radiation) may be applied concomitantly with the pulses of light. Nevertheless, this is not a limitation, and embodiments where the total intensity of this non-optical energy is at most 10% of the total electromagnetic radiation intensity are within the scope of the present invention. Typically, no RF radiation is applied, and only light (coherent and/or incoherent) is applied, though this is not to be construed as a limitation.

As noted above, various parameters may optionally varied in time, for example, repetition rate, pulse shape, pulse width, etc.

It is noted that in various embodiments, the electromagnetic radiation including the light pulse is applied so as to remove the hair (temporary and/or permanent hair removal) without burning the surrounding tissue/skin and/or leaving the surrounding tissue/skin free of injury.

Additional Discussion about Treatment Protocols

In some embodiments, the treating of the patient comprises the steps: (i) identifying a region of the patient where hair follicles are present (or a region from which it is desired to damage hair follicles; (ii) apply the electromagnetic radiation comprises a plurality of incoherent and/or coherent light pulses; (iii) allow the hair follicles to be damaged by the applied electromagnetic radiation.

Concomitant Application of Pulsed Radiation and Continuous Wave Radiation (CW)

Figure 4:
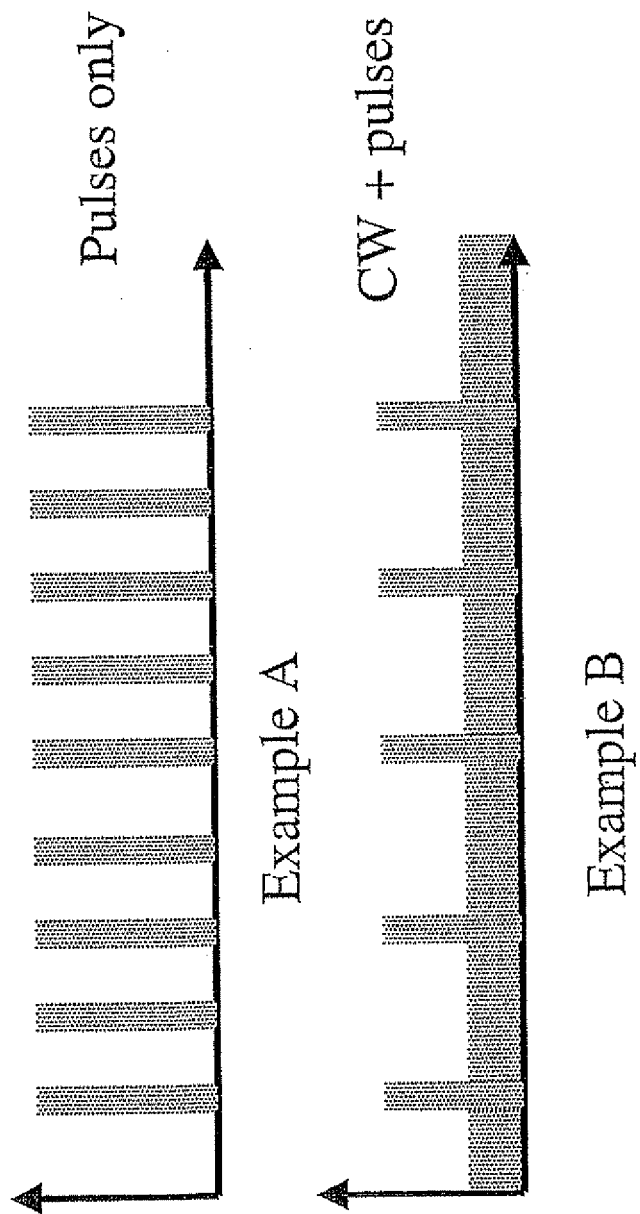
FIG. 4 provides a block diagram describing energy intensity as a function of time for exemplary treatment protocols.

FIG. 4 illustrates that when delivering optical radiation at a 'high average power' (i.e. sufficient to heat the dermis and to remove the hair) may be accomplished in several different ways. In example A of FIG. 4, a series of low-fluence pulses (for example, at most 20 J/cm^2 per pulse, for example, at most 15 or 10 J/cm^2 per pulse) (for example, at least 1 J/cm^20 per pulse) are rapidly (for example, at least 3 HZ, for example at least 4 HZ, for example, at least 5 HZ, for example, at least 8 HZ, for example, about 10 HZ) delivered to the skin of the patient. By delivering 'low fluence pulses' rapidly, it is possible to heat the dermis of the patient while localizing a certain amount of energy to the hair follicle so to facilitate removal the hair. In example B of FIG. 4, CW energy (or alternatively, a series of 'long pulses') is delivered concomitantly with the 'short pulses.' According to example B, the fluence of each individual short pulse may be less than the fluence in example A and/or the repetition rate of delivery of the individual short pulses may be less than in example A. Nevertheless, the overall 'average energy' is still sufficient to heat the dermis of the patient as described above. It is appreciated that for some examples, if the average energy of the CW radiation is increased, the energy delivered by the 'short pulse' may be decreased while the total amount of delivered average energy may remain 'high.'

Handpiece or Applicator Speed

Not wishing to be bound by any theory, it is noted that use of a relatively 'high' pulse delivery rate or frequency allows for application of light pulses via a handpiece that moves over the surface of the skin at a relatively 'high' velocity. This is because more individual pulses are delivered in a given period of time when the pulse delivery rate is higher, and thus, even the handpiece speed is relatively 'high,' a given hair follicle may still receive a minimum number of pulses.

In exemplary embodiments, on average, each hair follicle within a given treatment region (for example, a given treatment region of at least 1 cm^2, or at least 5 cm^2, or at least 10 cm^2, or at least 50 cm^2) receives between 10 and 15 pulses. It is recognized that depending on the specific application, there are some clinical situations where, for example, a given follicle is subject to at least 5 pulses, at most 20 pulses or any other number of pulses.

In some embodiments, the application of the plurality of light pulses is carried out via an applicator or handpiece (for example, an applicator that concomitantly provides cooling including but not limited to contact cooling) that moves or 'glides' over the surface of the treatment surface (i.e. over the surface of the skin) at a velocity that is, on average, at least 3 cm/sec (or at least 4 cm/sec, or approximately 5 cm/sec) during the time period that the plurality of light pulses are delivered at a given minimum average repetition rate (for example, during a time period where at least 10 pulses are delivered, or a time period that at least 20 pulses are delivered, or a time period that at least 50 pulses are delivered, or a time period that at least 75 pulses are delivered, or a time period a that at least 100 pulses are delivered.

As used herein, the 'velocity' of an applicator or handpiece refers to the velocity of a fixed point on the applicator or handpiece (for example, a center of mass, or in another example, a fixed point on an energy treatment surface) relative to the treatment region or skin as the applicator or handpiece moves over the surface of the treatment region or skin (for example, parallel to the local plane of the treatment region).

It is recognized that in different applications, the minimum or average velocity of the handpiece required during application or delivery of the light pulses may vary depending on the application—i.e. depending on parameters such as the repetition rate, the spot area, the level of aggressiveness of treatment required, etc.

Thus, in one example, if the repetition rate is higher, it is possible to deliver the light pulses from a handpiece or applicator having a higher velocity during the time of pulse delivery. In another example, a greater spot area will also allow a higher handpiece or applicator velocity.

In some embodiments, the average handpiece velocity during the time of pulse delivery (for either laser or incoherent light) is at least 3 cm/see, at least 4 cm/sec, or about 5 cm/sec. In some embodiments, the average handpiece or applicator velocity v is determined such that the ratio $(v^2)/[(freq)^2*(spot)]$ (where v is the velocity of the handpiece or applicator in cm/sec, spot is the spot area in $cm^2$) is at least 0.1, or at least 0.3, or at least 0.5, or at least 0.7 or at least 1, during the time period of delivery of the plurality of pulses of light (i.e. coherent or incoherent light).

Not wishing to be bound by theory, it is noted that in some embodiments, the practitioner treating the patient for hair removal may elect to employ a 'faster' or 'higher' velocity in order to provide a faster hair removal treatment.

Sequential Treatments of Sub-Regions of a Treatment Region

Figure 5B:
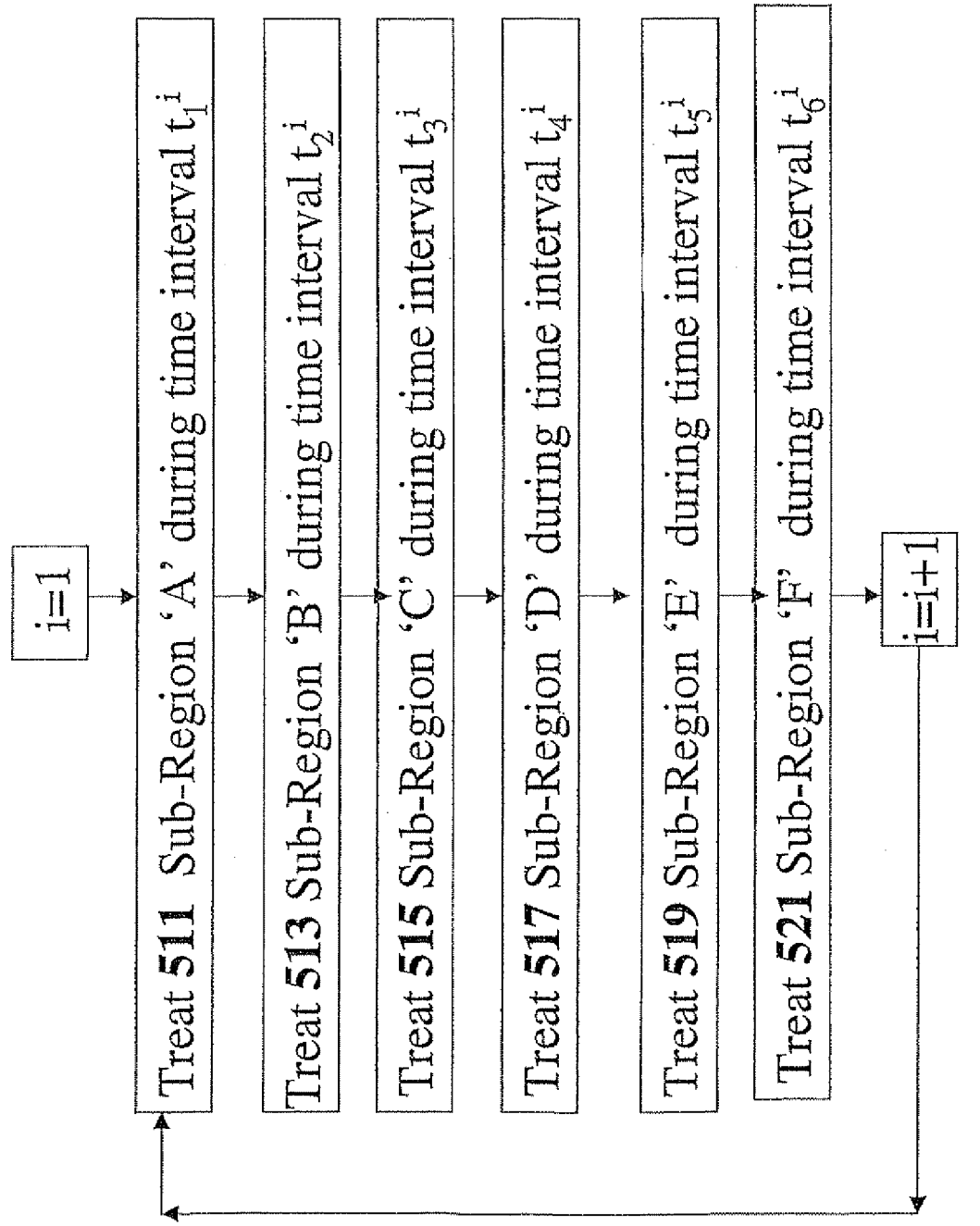
FIG. 5B provides a block diagram of an exemplary technique for treating various sub-regions of a treatment region.

FIG. 5A provides an illustration of an exemplary treatment region 500. It is noted that each of the sub-regions is a mathematical construct the example of FIG. 5A, each sub-region has a rectangular shape (and the overall treatment region 500 has a rectangular shape), though this is not to be construed as a limitation. According to the example of FIGS. 5A-5B, the practitioner providing hair-removal treatment to the patient applies pulses of light to different areas or sub-regions of the treatment region 500, for example, by moving a handpiece for delivering light pulses across the treatment region.

Thus, the treatment may be applied sequentially. In one particular example, during a course of treatment of treatment region 500, first sub-region 'A' 502 is treated 511 with a plurality of pulses of light; then first sub-region 'B' 504 is treated 513 with a plurality of pulses of light; then first sub-region 'C' 506 is treated 515 with a plurality of pulses of light; then first sub-region 'D' 508 is treated 517 with a plurality of pulses of light; ten first sub-region 'B' 510 is treated 519 with a plurality of pulses of light.

This process may be repeated any number of times. As shown in FIG. 5A, subscript i indicates the ith time the treatment of a given sub-region is carried out.

In the example of FIGS. 5A-5B, when a given sub-region is being treated, other sub-regions are not being tried (i.e. because the handpiece or applicator is at another location). Thus, sub-region 'A' is treated first during time interval $t_1^1$. Then during a 'resting' time interval including the intervals $t_2^1, t_3^1, t_4^1, t_5^1$ and, $t_1^6$ the applicator is treating other sub-regions (i.e. sub-regions 'B' through F'). Thus, during this 'resting' time interval, sub-region 'A' 502 does not receive pulses of light. Subsequently, during time interval, $t_1^2$, sub-region 'A' 502 once again is subjected 511 to a plurality of pulses of light.

Thus, the process described in FIG. 5B is one particular example of 'intermittent' application of pulses of light (i.e. each sub-region is intermittently subjected to a plurality of light pulses), which is described below.

Intermittent Application of Pulse of Light to a Given Location(s) on the Skin of a Patient to Facilitate Removal of Hair In some embodiments, not all pulses are delivered to a given location on the skin or a given hair follicle continuously or at once.

Thus, as described with reference to FIGS. 5A-5B, it is possible that a given first sub-region will be treated with a number of pulses, after which a second sub-region will be treated (for example, by moving the applicator or handpiece from the first to the second sub-region, for example, by gliding the applicator over the skin of the treated region to reach the second sub-region), after which the first sub-region will receive additional pulses of light.

Alternatively or additionally, in another example of 'intermittent' application of light pulses, a certain number of pulses may be delivered to a certain region, after which, for a period of time, no pulses are delivered to a treatment region (for example, the operate may temporarily stop pulse delivery, for example, using a foot-pedal), after which, once again, a certain number of pulses are delivered.

Furthermore, it is appreciated that in some embodiments, the speed of the applicator may be a function of the size of the region treated.

Figure 6:
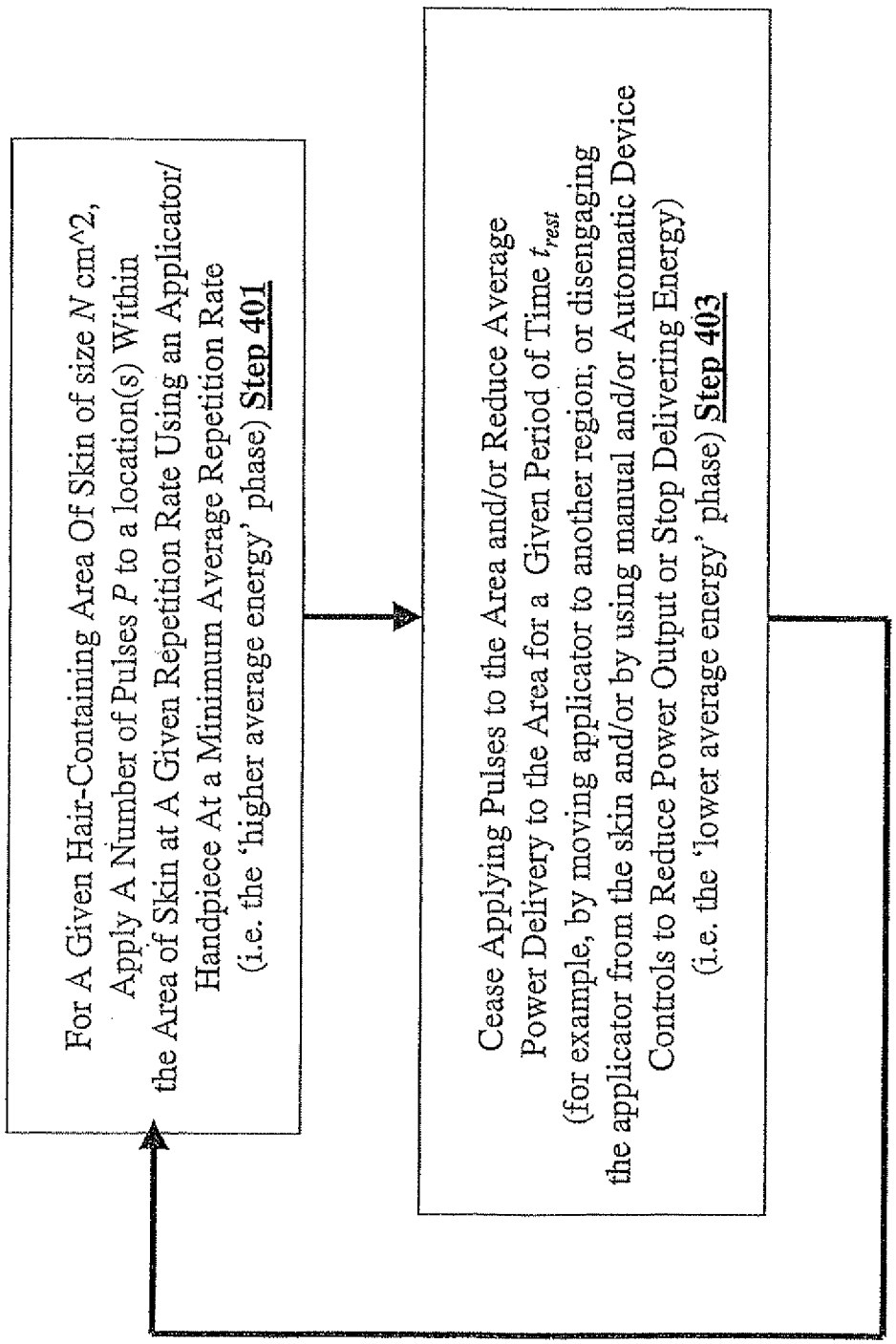
FIG. 6 provides a flow chart diagram of an exemplary procedure for treating a given location or area of tissue such as skin.

FIG. 6 provides a flow chart diagram of an exemplary procedure where a given location or area of tissue is intermittently subjected to applied light pulses—i.e. light pulses are applied over a first period of time (step 401), after which, during a second period of time (step 403) the given location or area of tissue does not receive the light pulses, after which, during a third period of time (i.e. repetition of step 401), the given location or area of tissue once again is subjected to the applied light pulses. Steps 401 and 403 may repeated any number of times to facilitate removal of hair from the given location or area.

Thus, in step 401, a series of light pulses are applied to delivered (i.e. comprising a minimum number of pulses P) at a given repetition rate. In one example, the light pulses are coherent light pulses having an average fluence that is at most 20 $J/cm^2$ per pulse and a least 0.5 $J/cm^2$ per pulse. In another example, the light pulses are incoherent light pulses (for example, from a flash lamp) having an average fluence that is less than 8 $J/cm^2$ per pulse and a least 0.5 $J/cm^2$ per pulse.

As used herein, delivering or applying one or more pulses of light (i.e. incoherent or coherent) to an area or region may include delivering the pulses to one or more locations within the area or region.

It is noted in some embodiments, the number of pulses P delivered to the area or region (i.e. to one or more locations within the area or region) in step 401 depends on the size of the area, where a larger area may receive more pulses due, for example, to the greater 'capacity' for the larger area to receive pulses at more locations within the larger area.

Thus, in one example, if the area of tissue is of size N $cm^2$ (i.e. has a surface area that is N $cm^2$), the number of pulses delivered in step 401 is at least the smallest integer that is greater than 1.5 N.

According to this example, the value of N may be in the range between 1 and 20, between 1.5 and 15, between 2 and 15, and in other sub-ranges.

In one specific example, an area of tissue of size 1 $cm^2$ may receive 2 pulses in a given 'pass' of the handpiece (i.e. during one instance of step 401). Similarly, in this example, an area of tissue of size 4 $cm^2$ may, in this specific example, receive 8 pulses in a given 'pass' of the handpiece.

Referring now to step 403, it is noted that after applying the at least P light pulses, the region or area (which may or may not be a sub-region of a larger treatment region) may be subjected to a resting phase where either no light pulses are delivered (i.e. to any location within the region or area) or only light having a reduced average power is applied or delivered to the region or area.

During the time period of step 403, the given region or area may be allowed to cool before repetition of step 401. This may be useful for providing a safe treatment.

In one example, where the applicator is applying energy elsewhere during the time period of step 403, no energy whatsoever need to be applied during the resting phase. This was described in FIGS. 4A-4B. Thus, for sub-region 'A' 502, the first execution of step 401 is carried out during time interval $t_1^1$. The first execution of step 403 is carried out during a time interval including time intervals $t_2^1, t_3^1, t_4^1, t_5^1$ and, $t_1^6$. The second execution of step 401 is carried out during time interval $t_1^2$.

For subregion 'B' 502, the first execution of step 401 is carried out during time interval $t_2^1$. The first execution of step 403 is carried out during a time interval including time intervals $t_3^1, t_4^1, t_5^1, t_1^6$ and $t_1^2$. The second execution of step 401 is carried out during time interval $t_2^2$.

It is noted that in various embodiments, this resting phase may be a 'no energy application phase' or a 'relatively low application of energy phase.'

In one example, during the 'resting phase' of step 403, an average power of the light (either the total amount of light or the amount of light in the region of the spectrum between 750 nm and 1500 nm) delivered (for example, delivered by the handpiece or applicator used to deliver, i.e. in step 401, the plurality of light pulses) does not exceed some 'low power' number—for example, does not exceed, say 30 Watts, or does not exceed 20 Watts, or does not exceed 10 Watts, or does not exceed 5 Watts.

In different embodiments, the duration of the 'resting' phase varies, for example, in accordance with a desired level of aggressiveness of treatment and/or the size of the overall 'treatment' region and/or physical parameters of the patient (for example, hair or skin color) and/or one or more various factors.

The skilled practitioner applying the treatment determine the length of the 'resting' phase according to a number of examples Thus, in different examples, the duration of the 'resting phase' of step 403 lasts for a minimum time that may depend on one more factors. Thus, for example, a given hair follicle may be subjected to the 'rest phase' for an amount of time that is least a few seconds and at most a period of time on the order of magnitude of a duration of a hair removal treatment—i.e. at most some number of minutes (for example, at most 20 minutes, or 30 minutes or an 60 minutes).

In one example, for example similar to the example of FIG. 5A, the length of the resting period may be influenced by the size of a given sub-region relative to the size of an overall treatment region. Thus, if the size of a given sub-region is small relative to the size of the overall treatment region, this may increase the length of time of the 'resting period' of step 403. If the of a given sub-region is larger relative to the size of the overall treatment region, this may decrease the length of time of the 'resting period' of step 403

It is noted that the total number of pulses delivered may depend on the size of the treatment region 500. In one example, the device may be pre-configured to deliver at least a certain number of pulses (or programmed to deliver any number of pulses), for example, at least 15, at least 30, at least 50, at least 100, and at least 500. Furthermore, in different examples, the user or practitioner providing the hair removal treatment may have a control to stop deliver of pulses (temporarily or altogether).

The following examples are to be considered merely as illustrative and non-limiting in nature. It will be apparent to one skilled in the art to which the present invention pertains that many modifications, permutations, and variations may be made without departing from the scope of the invention.

EXAMPLES

Various experiments were conducted by the present inventors to demonstrate human hair removal by applying optical radiation in accordance with one or more teachings disclosed herein. In Examples 1-2, some of the conducted experiments are described. In Example 3, additional exemplary protocols and device configuration parameters are related to incoherent light described.

Example 1

Hair Removal Using a Diode Laser

The present inventor has constructed an exemplary diode laser hair removal device, and has configured this device in accordance with certain teachings of the present invention. The present inventor has conducted certain experiments to illustrate hair removal using this aforementioned device.

Table 1, shown below, lists various optical fields configuration parameters that were used during one particular experiment. During this experiment, a series of square pulses were applied to the skin, where the time between pulse pairs was equal for all pulse pairs.

| Parameter | Value |
| --- | --- |
| Wavelength | 810 nm |
| Fluence | 10 J/cm$^2$ per pulse |
| Pulse Length | 22 ms |
| Spot Area | 1.0 cm$^2$ |
| Pulse frequency (rep rate) | 10 pulses/second |
| Peak power | 450 watts |
| Average power | ~100 watts |

After application of the plurality of light pulses, it was observed that the hair was removed. For this particular set of experiments, it was observed after 3 months that there was no significant re-growth of hair in the treated region (i.e. re-growth rate of less than 30%) for at least 3 months after application of the light pulses. It is anticipated that the time where there is no significant regrowth of hair is not limited to the currently-observed 3 months, and will continue in the future.

Example 2

Hair Removal Using Incoherent Intense Pulsed Light

The present inventor has constructed an exemplary flashlamp hair removal device, and has configured this device in accordance with certain teachings of the present invention. The present inventor has conducted certain experiments to illustrate hair removal using this aforementioned device.

In the exemplary device, light having a wavelength of less than 780 nm and greater than 1300 nm was filtered using low-pass filters.

Table 2, shown below, lists various optical fields configuration parameters that were used during one particular experiment. During this experiment, a series of square pulses were applied to the skin, where the time between pulse pairs was equal for all pulse pairs.

| Parameter | Value |
|---|---|
| Fluence | 5 J/cm^2 |
| Pulse Duration | 6 ms |
| Spot Area | 6.4 cm^2 |
| Pulse frequency (rep rate) | 3 pulses/second |
| Peak power | 5 * 1/0.006 * 6.4 = 5,330 W |
| Average power | 5 × 6.4 × 3 = 96 W |

Example 3

Hair Removal Using Incoherent Intense Pulsed Light

Example 3 describes additional device or treatment non-limiting parameters related to incoherent light (for example, IPL or flash).

| Parameter | Value |
|---|---|
| Fluence | 2 J/cm^2 |
| Pulse Duration | 2 ms |
| Spot Area | 6.4 cm^2 |
| Pulse frequency (rep rate) | 10 pulses/second |
| Peak power | 2 * 1/0.002 * 6.4 = 6,400 W |
| Average power | 2 × 6.4 × 10 = 128 W |

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A method of damaging hair follicles in a region of skin having a plurality of hair follicles, the method comprising:
 moving an applicator over the region of skin in order to apply, from the moving applicator, electromagnetic energy comprising a plurality of pulses of coherent light, wherein:
 (i) the wavelength of the light pulses lies within a range from 750 nm to 1500 nm,
 (ii) an average fluence per pulse of said plurality of pulses lies in a range from 3 J/cm² to 20 J/cm²;
 (iii) an average repetition rate of said plurality of pulses is at least 3 Hz and at most 20 Hz; and
 (iv) an average pulse duration of said light pulses is at least 10 milliseconds and at most 30 milliseconds,
 the pulses of coherent light being operative to heat the dermis of the skin to a temperature that is at least 42° C. and does not exceed 50° C., wherein (A) an average power density per square centimeter of said applied electromagnetic energy is at least 75 watts/cm²; and (B) a ratio between a peak power and an average power of said pulses of coherent light is at least 2.

2. A method of damaging hair follicles in a region of skin having a plurality of hair follicles, the method comprising:
 moving an applicator over the region of skin in order to apply, from the moving applicator, electromagnetic energy comprising a plurality of pulses of coherent light, wherein:
 (i) the wavelength of the light pulses lies within a range from 750 nm to 1500 nm,
 (ii) an average fluence per pulse of said plurality of pulses lies in a range from 3 J/cm² to 20 J/cm²;
 (iii) an average repetition rate of said plurality of pulses is at least 3 Hz and at most 20 Hz; and
 (iv) an average pulse duration of said light pulses is at least 10 milliseconds and at most 30 milliseconds,
 the pulses of coherent light being operative to heat the dermis of the skin to a temperature that is at least 42° C. and does not exceed 50° C., wherein a ratio between a peak power and an average power of said pulses of coherent light is at least 2.

3. A method as claimed in claim 2, wherein a ratio between a peak power and an average power of said pulses of coherent light is at most 10.

4. A method of damaging hair follicles in a region of skin having a plurality of hair follicles, the method comprising:
 moving an applicator over the region of skin in order to apply, from the moving applicator, electromagnetic energy comprising a plurality of pulses of coherent light, wherein:
 (i) the wavelength of the light pulses lies within a range from 750 nm to 1500 nm,
 (ii) an average fluence per pulse of said plurality of pulses lies in a range from 3 J/cm² to 20 J/cm²;
 (iii) an average repetition rate of said plurality of pulses is at least 3 Hz and at most 20 Hz; and
 (iv) an average pulse duration of said light pulses is at least 10 milliseconds and at most 30 milliseconds, the pulses of coherent light being operative to heat the dermis of the skin to a temperature that is at least 42° C. and does not exceed 50° C., wherein a ratio between a peak power and an average power of said pulses of coherent light is at most 10.

* * * * *